US009983155B2

(12) United States Patent
Knight et al.

(10) Patent No.: US 9,983,155 B2
(45) Date of Patent: May 29, 2018

(54) METHOD AND APPARATUS FOR GENERATING THERMAL MELTING CURVES IN A MICROFLUIDIC DEVICE

(71) Applicant: Canon U.S. Life Sciences, Inc., Rockville, MD (US)

(72) Inventors: Ivor T. Knight, North Arlington, VA (US); Deborah John Boles, Cary, NC (US); Aaron Rulison, Los Altos, CA (US); Wesley B. Dong, Belmont, CA (US); Andrew Fabans, Los Gatos, CA (US); Allen Boronkay, San Jose, CA (US); Edward Donlon, San Jose, CA (US); Robert Moti, San Jose, CA (US); Michael Slater, Modesto, CA (US); Steven A. Sundberg, San Francisco, CA (US); Michael R. Knapp, Palo Alto, CA (US)

(73) Assignees: Canon U.S. Life Sciences, Inc., Rockville, MD (US); CALIPER LIFE SCIENCES, INC., Mountain View, CA (US)

( * ) Notice: Subject to any disclaimer, the term of this patent is extended or adjusted under 35 U.S.C. 154(b) by 27 days.

(21) Appl. No.: 13/840,994

(22) Filed: Mar. 15, 2013

(65) Prior Publication Data
US 2014/0093879 A1 Apr. 3, 2014

Related U.S. Application Data

(63) Continuation of application No. 13/840,994, filed on Apr. 11, 2012, now Pat. No. 9,376,718, which is a continuation of application No. 13/444,502, filed on Feb. 9, 2006, now Pat. No. 8,900,811, which is a continuation-in-part of application No. 11/352,452, filed on Jan. 11, 2005, now abandoned, which is a continuation of application No. 11/032,749, filed on Nov. 15, 2001, now abandoned.

(60) Provisional application No. 10/003,472, filed on Nov. 16, 2000.

(51) Int. Cl.
| | |
|---|---|
| *G01N 25/04* | (2006.01) |
| *B01L 3/00* | (2006.01) |
| *B01L 7/00* | (2006.01) |
| *C12Q 1/68* | (2018.01) |
| *G01N 21/33* | (2006.01) |
| *G01N 21/64* | (2006.01) |

(52) U.S. Cl.
CPC .......... *G01N 25/04* (2013.01); *B01L 3/5027* (2013.01); *B01L 3/50273* (2013.01); *B01L 3/502715* (2013.01); *B01L 7/52* (2013.01); *B01L 7/525* (2013.01); *C12Q 1/68* (2013.01); *C12Q 1/686* (2013.01); *C12Q 1/6844* (2013.01); *C12Q 1/6862* (2013.01); *G01N 21/33* (2013.01); *G01N 21/6428* (2013.01); *B01L 2200/10* (2013.01); *B01L 2300/0627* (2013.01); *B01L 2300/0816* (2013.01); *B01L 2300/14* (2013.01); *B01L 2300/18* (2013.01); *B01L 2300/1833* (2013.01); *B01L 2400/0409* (2013.01); *B01L 2400/0415* (2013.01); *B01L 2400/0487* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 5,271,724 | A | 12/1993 | Van Lintel |
| 5,277,566 | A | 1/1994 | Augustin |
| 5,375,979 | A | 12/1994 | Trah |
| 5,498,392 | A | 3/1996 | Wilding |
| 5,600,690 | A | 2/1997 | Weems et al. |
| 5,679,516 | A | 10/1997 | Okamoto |
| 5,871,908 | A | 2/1999 | Henco |
| 5,942,443 | A | 8/1999 | Parce |
| 5,965,410 | A | 10/1999 | Chow |
| 6,132,580 | A | 10/2000 | Mathies |
| 6,140,054 | A | 10/2000 | Wittwer et al. |
| 6,174,670 | B1 | 1/2001 | Wittwer et al. |
| 6,358,387 | B1 | 3/2002 | Kopf-Sill et al. |
| 6,403,338 | B1 | 6/2002 | Kopf-Sill |
| 6,406,893 | B1 | 6/2002 | Knapp |
| 6,472,156 | B1 | 10/2002 | Wittwer et al. |
| 6,551,841 | B1 | 4/2003 | Wilding |
| 6,569,627 | B2 | 5/2003 | Wittwer et al. |

(Continued)

FOREIGN PATENT DOCUMENTS

| | | |
|---|---|---|
| WO | 1994/005414 A1 | 3/1994 |
| WO | 1996/004547 A1 | 2/1996 |

(Continued)

OTHER PUBLICATIONS

Ross et al, "Temperature measurement in microfluidic systems using a temperature-dependent fluorescent dye" Analytical Chemistry Sep. 1, 2001 United States, vol. 73, No. 17.
Sinton: "Microscale flow visualization" Microfluidics and Nanofluidics, vol. 1, No. 1, Aug. 18, 2004, pp. 2-21.
Zhang et al: "PCR Microfluidic devices for DNA amplification" Biotechnology Advances, vol. 24, No. 3, May 2006, pp. 243-284.
Breuer, Kenneth S., "Micro-and-Nano-Scale Diagnostic Techniques" Jan. 15, 2005, Springer, New York, XP002446772, p. 113-154.
Clayton, Julie, "Go with the Microflow," Nature Methods, Aug. 2005, vol. 2 No. 8, 621-627.

(Continued)

*Primary Examiner* — David C Thomas
(74) *Attorney, Agent, or Firm* — Rothwell, Figg, Ernst & Manbeck, P.C.

(57) ABSTRACT

The present invention provides novel methods and devices that employ microfluidic technology to generate molecular melt curves. In particular, the devices and methods in accordance with the invention are useful in providing for the analysis of PCR amplification products.

28 Claims, 10 Drawing Sheets

(56) References Cited

U.S. PATENT DOCUMENTS

| | | | |
|---|---|---|---|
| 6,670,133 B2* | 12/2003 | Knapp et al. | 435/6.19 |
| 8,058,054 B2 | 11/2011 | Owen et al. | |
| 9,114,398 B2* | 8/2015 | Knight | B01L 3/5027 |
| 2001/0036637 A1 | 11/2001 | Fujita et al. | |
| 2001/0041357 A1 | 11/2001 | Fouillet et al. | |
| 2002/0119442 A1 | 6/2002 | Dunlop et al. | |
| 2002/0197630 A1 | 12/2002 | Knapp | |
| 2003/0224434 A1 | 12/2003 | Wittwer | |
| 2004/0005720 A1 | 1/2004 | Cremer et al. | |
| 2005/0042039 A1 | 2/2005 | Knapp | |
| 2005/0202470 A1 | 9/2005 | Sundberg et al. | |
| 2005/0282224 A1 | 12/2005 | Fouillet et al. | |
| 2006/0011478 A1* | 1/2006 | Fouillet | G01N 35/08 204/451 |

FOREIGN PATENT DOCUMENTS

| | | |
|---|---|---|
| WO | 1997/002357 A1 | 1/1997 |
| WO | 1998/045481 A1 | 10/1998 |
| WO | 1998/046438 A1 | 10/1998 |
| WO | 1998/049548 A1 | 11/1998 |
| WO | 1999/12016 | 3/1999 |
| WO | 1999/039190 A1 | 8/1999 |
| WO | 2000/043766 A1 | 7/2000 |
| WO | 2000/045170 A2 | 8/2000 |
| WO | 2000/045172 A1 | 8/2000 |
| WO | 2000/060108 A1 | 10/2000 |
| WO | 2000/070080 A1 | 11/2000 |
| WO | 2002/022878 A1 | 3/2002 |
| WO | 2004/078316 A1 | 9/2004 |

OTHER PUBLICATIONS

Lui, Robin Hui et al., "Self-Contained, Fully Integrated Biochip for Sample Preparation, Polymerase Chain Reaction Amplification, and DNA Microarray Detection, Analytical Chemistry," Apr. 1-11, 2006, vol. 76, No. 7, 1824-1830.
Ouellette, Jennifer, "A New Wave of Microfluidic Devices," The Industrial Physicist, American Institute of Physics, Aug./Sep. 2003, 14-17.
Rida, A. and M.A.M. Gijs, "Manipulation of Self-Assembled Structures of Magnetic Beads for Microfluidic Mixing and Assaying," Analytical Chemistry, Nov. 1, 2004, vol. 76, No. 21, 6239-6246.
Rida, A and M.A.M. Gijs, "Long-Range Transport of Magnetic Microbeads Using Simple Planar Coils Placed in a Uniform Magnetistatic Field." Applied Physic Letters, Sep. 22, 2003, vol. 82, No. 12, 2396-2398.
Shastry, M.C. Ramach!.ndra et al. "A Continuous-Flow Capillary Mixing Method to Monitor Reactions on the Microsecond Time Scale." Biophysical Journal, May 1998, vol. 74 No. 5, 2714-2721.
Barcelo F. et al. (1990) "A scanning calorimetric study of natural DNA and antitumoral anthracycline antibiotic-DNA complexes," Chem Biol Interact, 74(3):315-324.
Brandts, J. et al. (1990) "Study of strong to ultratight protein interactions using differential scanning calorimetry," Biochem 29:6927-2940.
Brandts, J. et al. (1990) American Laboratory 22:3041+.
Chavan, A. et al. (1994) "Interaction of nucleotides with acidic fibroblast growth factor (FGF-1) Biochem," 33 (23):7193-7202.
Checovich et al. (1995) "Fluorescence polarization-a new tool for cell and molecular biology," (product review) Nature 375:354-256.
Clegg, R. et al. (1994) "Observing the helical geometry of double-stranded DNA in solution by fluorescence resonance energy transfer." Proc Natl Acad Sci USA 90(7):2994-2998.
Dandliker and De Saussure (1970) (Review Article) "Fluorescence polarization in immunochemistry," Immunochemlstry 7:799.
Dandliker and Feigen(1961) "Quantification of the antigen-antibody reaction by the polarization of fluorescence," Biochem Biophys Res Commun 5:299.
Dandliker W. 8. et al. (1973) "Fluorescence polarization immunoassay. Theory and experimentel method," Immunochemistry 10:219.

Devlin et al. (1993) "Homogeneous detection of nucleic acids by transient-state polarized fluorescence," Clin Chem 39:1939.
Gonzalez., M. et al., "Interaction of Biotin with Streptavidin," J Biol Chem, (1997) 272(17): 11288-11294.
Haugland, Handbook or Fluorescent Probes and Research Chemicals Published by Molecular Probes, Inc., (1996), Chapter 13, Eugene, OR.
Hefti, J. Etal."Sensitive detection method of dielectric dispersions in aqueous-based, surface-bound macromolecular structures using microwave spectroscopy," Applied Phys Letters, (1999), 75(12):1802-1804.
Jiskoot M. et al. (1991) "Preparation and application or a fluorescein-labeled peptide for determining the affinity constant of a monoclonal antibody-hapten complex by fluorescence polarization," Anal Biochem 196:421.
Johnson, W. (1990) "Protein Seeondary Structure and Circular Dichroism: A Practical Gulide." Proteins 7:205-214.
Kleanthous, C. M. et al. (1991) "Stabilization of the shikimate pathway enzyme dehydroquinase by covalently bound ligand," J Biol Chem, 286(17):10893-10898.
Kopp. M. et al. (1998) "Chemical amplification: continuous-flow PCR on a chip." Science 280(5366): 1046-1048.
Kumke et al. (1995) "Hybridization of fluorescein-labeled DNA oligomers detected by fluorescence anisotropy with protein binding enhancement." Anal Chem 67(21):3945-3951.
Lee, M. et al. (1993) "In vitro cytotoxicity of GC sequence directed alkylating agents related to distamycin," J Med Chem 36(7):863-870.
Levison, S. A. et al. (1976) "Fluorescence polarization measurement of the hormone-binding aite interaction," Endocrinology 99:1129.
Morton, A. et al., "Energetic origins of specificity of ligand binding in an Interior nonpolar cavity of T4 lysozyme," Blochem (1995) 34(27):8564-8575.
Murakami et al., "Fluorescent-labeled oligonucleotide probes detection of hybrid formation in solution by fluorescence polarization spectroscopy." Nuc Acids Res (1991) 19:4097.
Nikiforov and Jeong, "Detection of Hybrid Formation between Peptide Nucleic Acids and DNA by Fluorescence Polarization in the Presence of Polylysine." Analytical Biochemistry (1999)275:248-253.
Ory, J. et al, "Studies of the Ligand Binding Reaction of Adipocyta Lipid Binding Protein Using Iha Fluorescent Probe 1,8-AnHinonaphlhalena-8-Sulfonale." Biophys (1999) 77:1107-1116.
Pilch, D. Etal., "Ligand-induced formation of nucleic acid triple helices," Proc Natl Acad Sci USA, (1994) 91 (20):9332-9336.
Ropson, I. et al .. Fluorescence spectral changes during the folding of intestinal fatty acid binding protein, Biochem, (1997) 36(38):8594-8601.
Schellman. J., Blopolymers (1975) 14:999-1018.
Schellman, J ., Blopolymers (1976) 15:999-1000.
Schonbrunn, E. et al, "Structural basis for the Interaction of the fluorescence probe 8-anlMno-1-naphthalene sulfonate (ANS) with the antibiotic target MurA" Proc Natl Acad Sci USA (2000) 97 (12):6345-6349.
Selvin, P., "The renaissance of fluorescence resonance energy transfer," Nat Struct Blol (2000) 7(9):730-734.
Tyagi, S. et al., "Molecular beacons: probes that fluoresce upon hybridiZation," Nat Bioteoh (1996) 14:303-308.
Tyagi, s. et al, "Multicolor molecular beacons for allele discrimination," Nat Biolach (1998)16:49-53.
Walker, J. et al, "Strand displacement amplification (SDA) and transient-state fluorescence polarization detection ot mycobacterium tuberculosis DNA," CUnical Chemistry (1996) 42(1):9-13.
Weber, P. et al .. "Structure-based design of Synthetic Azobenzene Ligands for Streptavldln," J Am Chem Soc (1994) 16:2717-2724.
Wei and Herron, "Use of synthetic peptides as tracer antigens in fluorescence polarization immunoassays of high molecular weighl analytes," Anal Chem (1993) 65:3372.
Woody, R., "Circular Dichroism of Peptides." The Peptides (1995) 7:14-114, Academic Press.

* cited by examiner

SEQUENCE LISTING

```
<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: first oligonucleotide strand of double stranded
      oligonucleotide for melting analysis
<220> FEATURE:
<221> NAME/KEY: misc_feature
<222> LOCATION: (1)..(1)
<223> OTHER INFORMATION: 5' nucleotide bound to fluoroscein

<400> SEQUENCE: 1
gcggcgggcc tgatgacaca gctactcctt ggatg                              35

<210> SEQ ID NO 2
<211> LENGTH: 35
<212> TYPE: DNA
<213> ORGANISM: Artificial Sequence
<220> FEATURE:
<223> OTHER INFORMATION: second oligonucleotide strand of double
      stranded oligonucleotide for melting analysis
<220> FEATURE:
<221> NAME/KEY: misc_feature
```

```
<222> LOCATION: (35)..(35)
<223> OTHER INFORMATION: 3' nucleotide bound to TAMRA

<400> SEQUENCE: 2
catccaagga gtagctgtgt catcaggccc gccgc                              35
```

METHOD AND APPARATUS FOR GENERATING THERMAL MELTING CURVES IN A MICROFLUIDIC DEVICE

CROSS-REFERENCES TO RELATED APPLICATIONS

Pursuant to 35 U.S.C. § § 119 and/or 120, and any other applicable statute or rule, this application is a continuation of U.S. Ser. No. 13/444,502 filed Apr. 11, 2012, which is a continuation of U.S. Ser. No. 11/352,452 filed Feb. 9, 2006, which is a continuation-in-part of U.S. Ser. No. 11/032,749, filed Jan. 11, 2005, which is a continuation of U.S. Ser. No. 10/003,472 filed Nov. 15, 2001, which claims priority to U.S. Ser. No. 60/249,578, filed on Nov. 16, 2000. The disclosures of all of those applications are incorporated herein by reference.

TECHNICAL FIELD

The present invention relates to the characterization of biological materials on a microfluidic device. More particularly, embodiments of the present invention are directed toward determining the thermal properties of biological materials on a microfluidic device.

BACKGROUND OF THE INVENTION

When carrying out chemical or biochemical analyses, assays, syntheses or preparations, a large number of separate manipulations are performed on the material or component to be assayed, including measuring, aliquotting, transferring, diluting, mixing, separating, detecting, incubating, etc. Microfluidic technology miniaturizes these manipulations and integrates them so that they can be executed within one or a few microfluidic devices.

For example, pioneering microfluidic methods of performing biological assays in microfluidic systems have been developed, such as those described by Parce et al. in U.S. Pat. No. 5,942,443 entitled "High Throughput Screening Assay Systems in Microscale Fluidic Devices", and Knapp et al. in PCT Publication No. WO 98/45481 entitled "Closed Loop Biochemical Analyzers". Additionally, microfluidic devices for performing temperature-mediated reactions have been explored by Stern in U.S. Pat. No. 6,670,153.

One type of biological assay of particular interest in many fields of science is the detection and quantification of binding between various molecules. For example, screening of numerous compounds or molecules to determine how they bind to one another or how they bind to a particular target molecule is extremely important in many areas of research. For example, screening of large libraries of molecules is often utilized in pharmaceutical research. "Combinatorial" libraries, composed of a collection of generated compounds, can be screened against a particular receptor to test for the presence of possible ligands and to quantify the binding of any possible ligands.

Various methods exist to characterize the binding between molecules. Many of those methods involve calorimetric analysis. Isothermal calorimetry (ITC) and differential scanning calorimetry (DSC) are examples of such methods. By measuring the thermal parameters of a binding reaction, calorimetry can be used to test for the presence of binding between the molecules by detecting a shift in the thermal denaturation of a molecule that occurs when another molecule is bound to it. The shift in the thermal denaturation of a molecule (which could be as expressed in a molecular melt curve) can be monitored via the fluorescence of an indicator dye that binds to only select conformational states of the molecule. Alternatively, in some cases the binding between molecules can be determined by changes in the intrinsic fluorescence of one of the molecules.

Characterization of the binding between molecules is also important tool in the characterization of nucleic acids. For example, Knapp et al. in U.S. Published Application No. 2002/0197630 entitled "Systems for High Throughput Genetic Analysis" discuss the use of melting curve analysis to detect single nucleotide polymorphisms (SNPs). Molecular melt curves (and differences between molecular melt curves) can also be used to detect and analyze sequence differences between nucleic acids. The thermal denaturation curve for nucleic acids can be monitored by, e-g., measuring thermal parameters, fluorescence of indicator dyes/molecules, fluorescence polarization, dielectric properties, or the like.

A welcome addition to the art would be a process that allows rapid binding assays to be performed on a microfluidic device with minimal use of compounds and reagents. The current invention describes and provides these and other features by providing methods and microfluidic devices for performing binding assays using molecular melt curves. These and other features of the invention will be made clear upon review of the following.

SUMMARY OF THE INVENTION

The present invention provides methods, systems, kits and devices for conducting binding assays using molecular melt curves in microfluidic devices. Molecule(s) to be assayed can be flowed through microchannels in the devices where the molecule(s) optionally are exposed to additional molecules constituting, e.g., fluorescence indicator molecules and/or binding partners of the molecule being assayed. The molecules involved are then heated (and/or cooled) and a detectable property of the molecules is measured over a range of temperatures. From the resulting data, a thermal property curve(s) is constructed which allows determination and quantification of the binding affinity of the molecules involved.

In one aspect, methods of generating a thermal property curve for at least one molecule in a microfluidic device are provided. The methods comprise flowing the molecule(s) into a microchannel, heating the molecule(s) in the microchannel, detecting at least one detectable property of the molecule(s) during the heating, and, generating a thermal property curve for the molecule(s) from such data. The methods provided involve observation of changes in at least one physical property of the one or more molecule(s), e.g., fluorescence, which results from, e.g., unfolding or denaturing, or from altering of one or more additional physical property of the molecule, in response to changes in temperature and as a result of binding.

The methods are applicable to numerous types of molecular interactions, including those of proteins, enzymes, nucleic acids (either double-stranded or single-stranded), ligands, peptide nucleic acids, cofactors, receptors, substrates, antibodies, antigens, polypeptides, etc., with one or more additional molecule or moiety. The methods of the invention are also applicable to molecules that comprise a complex of two or more molecules, e.g., an enzyme complexed to a second enzyme, a ligand, a peptide nucleic acid, a cofactor, a receptor, a substrate, or other such combinations.

In the methods of the invention, flowing typically comprises, e.g., transporting the molecule(s) of interest through at least one microchannel of the microfluidic device. This flowing can be done electrokinetically, by use of positive or negative pressures, by both electrokinetics and positive or negative pressure, by gravity, by capillary action, through displacement of fluid by expanding membranes, or by centripetal force. Flowing can involve either simultaneous or sequential transport of the molecules(s) through one or more microchannels. Alternatively, the methods of the invention can entail flowing a first molecule through one microchannel and one or more other molecule(s) through a second microchannel, e.g., where the various microchannels intersect with each other.

In the methods in accordance with the invention, heating comprises elevating the temperature of the molecule(s) for a selected period of time. This period of time can range, e.g., from about 0.1 second through to about 1.0 minute or more, from about 0.1 second to about 10 seconds or more, or from about 0.1 second to about 1.0 second or more, including all time periods in between. Optionally, heating can involve raising the temperature of the molecule(s) at a selected point in time after contacting a first molecule by a second molecule. This selected point in time can be from, e.g., about 0.1 second to about 1.0 minute or more, from about 0.1 second to about 10 seconds or more, or from about 0.1 second to about 1.0 second or more (including all time periods in between) after flowing the first molecule into the microchannel. Furthermore, temperature control in the methods can entail setting the temperature of the molecule(s) to a selected temperature that can be from, e.g., about 10° C. to about 100° C. or more, from about 10° C. to about 90° C. or more, or from about 10° C. to about 60° C. or more (including all temperatures in between).

In other methods in accordance with the invention, heating comprises elevating the temperature of the molecule(s) by continuously increasing the temperature of the molecule(s). For example, the temperature of the molecule(s) can be continuously increased at a rate in the range of 0.1° C./second to 1° C./second. Alternatively, the temperature of the molecule(s) can be continuously increased at a slower rate, such as a rate in the range of 0.01° C./second to 0.1° C./second, or at a faster rate, such as a rate in the range of 1° C./second to 10° C./second.

Heating the molecules optionally comprises elevating the temperature of the molecule(s) in the microchannel by either joule heating, non-joule heating, or both joule heating and non-joule heating. In one embodiment, joule heating is performed by flowing a selectable electric current through the microchannel, thereby elevating the temperature. Joule heating can occur over the entire length of the microchannel or over a selected portion of the microchannel. Joule heating can be applied to selected portions of microchannels by flowing a selectable electric current through a first section and a second section of a microchannel wherein the first section comprises a first cross-section and the second section comprises a second cross-section. Furthermore, the first cross-section is of a greater size than the second cross-section, which causes the second cross-section to have a higher electrical resistance than the first cross-section, and therefore a higher temperature than the first cross-section when the selectable electric current is applied. The level of joule heating can be controlled by changing the selectable current, the electrical resistance, or both the current and the resistance. The selectable current used for joule heating can include direct current, alternating current or a combination of direct current and alternating current. See, e.g., U.S. Pat. No. 5,965,410.

Optionally the heating used in the methods of the invention includes non-joule heating, e.g., through application of an internal or an external heat source. In one embodiment, the internal or external heat source includes a thermal heating block. Just as for joule heating, non-joule heating optionally occurs over the entire length of the microchannel or over a selected portion of the microchannel. For example, one or more regions of the microchannel can be proximal to one or more heating element.

Heating methods in accordance with the invention also encompass the application of a temperature gradient along the length of a portion of a microchannel. The temperature at one end of the length of the microchannel is controlled to a first selected temperature, and the temperature at the other end of the length is controlled to a second selected temperature, thus creating a continuous temperature gradient spanning the temperature range between the first and second selected temperatures. Once a steady state flow of fluid through the portion of the microchannel is established, a temperature gradient will be established within that fluid. When Joule heating is used, a temperature gradient can be established along the length of a microchannel by fabricating the channel so that it continuously and monotonically changes in cross-sectional area along its length, and then applying a single electric current through that length. One method of establishing a temperature gradient along the length of a microchannel when non-joule heating is employed is to place a thermal block in contact with the microchannel, and to establish a temperature gradient across the block in the direction corresponding to the length direction of the microchannel using heating or cooling elements.

In another aspect of the invention, the methods of detecting a property of the molecule(s) involved comprises detecting a level of fluorescence or emitted light from the molecule(s) that varies as a function of relative amounts of binding. In one configuration, the detecting of fluorescence involves a first molecule and a second molecule, wherein the first molecule is a fluorescence indicator dye or a fluorescence indicator molecule and the second molecule is the target molecule to be assayed. In one embodiment, the fluorescence indicator dye or fluorescence indicator molecule binds or associates with the second molecule by binding to hydrophobic or hydrophilic residues on the second molecule. The methods of detecting optionally further comprise exciting the fluorescence indicator dye or fluorescence indicator molecule to create an excited fluorescence indicator dye or excited fluorescence indicator molecule and discerning and measuring an emission or quenching event of the excited fluorescence indicator dye or fluorescence indicator molecule.

In an illustrative embodiment of a method involving detection of fluorescence involves a molecule that comprises a protein or a polypeptide. In this embodiment, the method of detecting further entails exciting amino acid residues such as tryptophan in the protein or polypeptide, thereby creating excited tryptophan residues. Discerning and measuring an emission or quenching event of the excited tryptophan residues is used to detect a property of the molecule(s) being assayed.

In addition, or separate from, fluorescence or emitted light detection, detecting a property of the molecule(s) being assayed may optionally comprise the use of, e.g., fluorescence spectroscopy involving, e.g., fluorescence polarization, fluorescence resonance energy transfer (FRET), fluorescence lifetime imaging microscopy, molecular beacons, fluorescence correlation spectroscopy (FCS), circular dichroism, or the like. Similarly, a change in the thermal parameters of a system involving the molecule(s) in the microchannel can be monitored (e.g., the change in the heat capacity is detected and measured). Additionally changes in dielectric properties can be followed and measured. Yet another method of detecting a property of the molecule(s) being assayed comprises monitoring the UV absorbance of the molecule(s).

Another aspect of the methods of the invention includes generating a thermal property curve. One embodiment of generating a thermal property curve includes providing one molecule comprising a fluorescence indicator dye or fluorescence indicator molecule, and at least a second molecule comprising one or more of: an enzyme, a ligand, a peptide nucleic acid, a cofactor, a receptor, a substrate, a protein, a polypeptide, a nucleic acid (either double-stranded or single-stranded), an antibody, an antigen, or an enzyme complex. A fluorescence of the first molecule in the presence of the second molecule as a function of temperature is measured and the resulting data is used to generate a thermal property curve.

An additional embodiment of generating the thermal property curve comprises measuring a change in the fluorescence of one molecule that is correlative or proportional to a change in a physical property of another molecule(s) due to a change in temperature. A further embodiment includes generating a thermal property curve control curve by measuring fluorescence of a first molecule in the presence of a second molecule as a function of temperature, where the first molecule is a fluorescence indicator dye or molecule and the second molecule is: a protein, a polypeptide, an enzyme, an enzyme complex, a nucleic acid (either single-stranded or double-stranded), a ligand, a peptide nucleic acid, a cofactor, a receptor, an antibody, an antigen, or a substrate.

In another embodiment, the methods of the invention include generating a thermal property curve from the fluorescence of a tryptophan on a first molecule comprising a tryptophan-containing protein, polypeptide, enzyme, or enzyme complex when the first molecule is in the presence of a second molecule comprising an enzyme, a ligand, a peptide nucleic acid, a cofactor, a receptor, a substrate, a protein, a polypeptide, a nucleic acid (either double-stranded or single-stranded), an antibody, an antigen, or an enzyme complex. The fluorescence of the tryptophan residues present in the first molecule while in the presence of the second molecule as a function of temperature is measured and the resulting data used to generate a thermal property curve. An additional element of generating the thermal property curve in this embodiment of the invention includes measuring the melting temperature of the second molecule. Optionally, a change in the fluorescence of the tryptophan residues is correlative or proportional to a change in the physical property of the second molecule due to a change in temperature. Optionally, a thermal property curve control curve is generated by measuring the fluorescence of the tryptophan residues of the first molecule in the absence of the second molecule, as a function of temperature.

In yet another embodiment, methods in accordance with the invention include generating a thermal property curve where a first molecule and at least a second molecule are proteins, polypeptides, enzymes, enzyme complexes, nucleic acids (both double-stranded and single-stranded), ligands, peptide nucleic acids, cofactors, receptors, antibodies, antigens, or substrates. In these embodiments, generating a thermal property curve comprises measuring a change in the thermal parameters of the system comprising the molecule(s) in the microchannel as a function of temperature when a first molecule is in the presence of at least a second molecule. An additional embodiment entails generating a control curve by measuring the change in the total free energy of the system as a function of temperature without the presence of a second molecule.

In an optional embodiment, the invention comprises methods to establish a reference temperature in a microfluidic channel through generation of thermal property curves for molecule(s) of known $T_m$ e.g., biotin, biotin-4-fluorescein, fluorescein biotin, avidin, streptavidin, neutravidin, or complementary double-stranded nucleic acids of known sequence and/or $T_m$, (which are optionally labeled differently on each strand as in FRET donor/acceptor-quencher pairs or otherwise labeled to indicate transition to the single-stranded state).

In another aspect, the invention includes microfluidic systems comprising a microfluidic device having body structure containing at least one fluidic microchannel; a fluid direction system for controllably moving reagents into and through the microchannel; at least one energy source for controllably heating the reagents in the microchannel; a source of a fluorescence indicator dye or fluorescence indicator molecule fluidly coupled to the microchannel; a source of one or more sample molecules to be assayed fluidly coupled to the microchannel; an excitation source for the fluorescence indicator dye or fluorescence indicator molecule; a detector proximal to the body structure for detecting a change in a physical property of the one or more sample molecules; and, a computer operably coupled to the detector, containing an instruction set for acquiring data from the detector and for constructing thermal melt curves and control curves from the data.

In another embodiment, the integrated system or microfluidic devices of the invention include a fluid direction system which, during operation, controllably determines the selection of one or more reagent(s) to be added to the microchannel; the amount of one or more reagent(s) to be added to the microchannel; the time at which one or more reagent(s) is to be added to the microchannel; and the speed at which one or more reagent(s) is to be added to the microchannel.

In another embodiment, the integrated system or microfluidic devices of the invention include at least one energy source which, during operation, elevates the temperature of the molecule(s) in the microchannel by either joule heating, non-joule heating or both joule heating and non-joule heating.

Joule heating in the integrated system or microfluidic device of the invention comprises the flow of a selectable electric current through the at least one microchannel, thereby elevating the temperature. Joule heating can be applied uniformly over the entire length of the microchannel, or at different levels at different portions of the microchannel. One method of heating different portions of the microchannel differently comprises flowing a selectable electric current through at least a first section of a microchannel and through at least a second section of a microchannel wherein the first section of the microchannel comprises a first cross-sectional area and the second section of the microchannel comprises a second cross-sectional area. The first cross-sectional area is typically greater than the second cross-sectional area, causing the second section to have a higher electrical resistance than the first section, and, therefore have more heat generated within it than in the first section when the selectable electric current is applied. Alternatively, a temperature gradient can be established across the length of the channel by continuously and monotonically changing the cross-sectional area of the channel. The level of joule heating is controlled by changing the selectable current, the electrical resistance of the fluid in the channel, or both the current and the resistance. The selectable current may comprise a direct current, an alternating current or a combination of direct current and alternating current.

Optionally, the integrated system or microfluidic device of the invention includes non-joule heating through an internal or external heat source. In some embodiments, the internal or external heat source may comprise one or more of a thermal heating block, Peltier device, resistive heating element, thermoelectric cooler, gas or liquid that transfers heat conductively or convectively. Just as for joule heating, non-joule heating optionally can produce a uniform temperature over the entire length of the microchannel, different temperatures within different portions of the microchannel, or a continuously varying temperature along the length of the microchannel.

In another embodiment of the invention, the integrated system or microfluidic device optionally provides at least one fluorescence indicator dye or fluorescence indicator molecule capable of binding to one or more hydrophobic amino acid residues, one or more hydrophilic amino acid residues, or a combination thereof, of another molecule. For example, the fluorescence indicator dye or fluorescence indicator molecule comprises, e.g., 1-analino-naphthalene-8-sulfonate. In another embodiment, the fluorescence indicator dye or fluorescence indicator molecule can intercalate into, or bind by another mechanism to, one or more nucleic acid polymers. In yet another embodiment, the fluorescence indicator molecule comprises at least one tryptophan residue.

In various embodiments, an integrated system or microfluidic device in accordance with the invention may comprise a high-through-put format, a low-throughput format, or a multiplex format. In many embodiments of the invention the excitation source for exciting the fluorescence indicator dye or fluorescence indicator molecule comprises a light source. For example, the light source may comprise one of more of a tungsten-halogen lamp, a xenon-arc lamp, a mercury lamp, a laser, an LED, or a fiber optic cable. Some embodiments of the integrated system comprise an array of light sources to excite fluorescence at a plurality of locations along the length of a microchannel in the microfluidic device.

In some embodiments, the integrated system determines a reference temperature in a microfluidic channels of the microfluidic device within the system through generation of thermal property curves for molecule(s) of known $T_m$, e.g., biotin, biotin-4-fluorescein, fluorescein biotin, avidin, streptavidin, neutravidin, or complementary double-stranded nucleic acids of known sequence and/or T, (which are optionally labeled differently on each strand as in FRET donor/acceptor-quencher pairs or otherwise labeled to indicate transition to the single-stranded state).

An integrated system in accordance with the invention may comprise one or more of the following types of optical detectors: a fiber optic probe, a charge coupled device, a fluorescence imaging camera, a photomultiplier, a photodiode, or a fluorescence polarization sensor. The system may also comprise an array of optical detectors to measure optical signals emanating from a plurality of locations along the length of a microchannel in the microfluidic device. Additionally, an integrated system in accordance with the invention may comprise one or more of the following types of temperature detectors: contact temperature detectors such as thermocouples, resistance temperature detectors, or thermistors; or non-contact temperature detectors such as IR thermometers or optical pyrometers. The system may also comprise an array of temperature detectors to measure the temperature at a plurality of locations along the length of a microchannel in the microfluidic device. The optical detector optionally has the ability to detect fluorescence or emitted light from an excited fluorescence indicator dye or molecule or optionally has the ability to detect a change in the thermal parameters of the system comprising the molecule(s) in the at least one microchannel.

Kits for performing one or more target independent and/or target dependent assay to produce the pre-screened libraries of the invention are also a feature of the invention.

DETAILED DESCRIPTION OF THE INVENTION

Figure 1A:
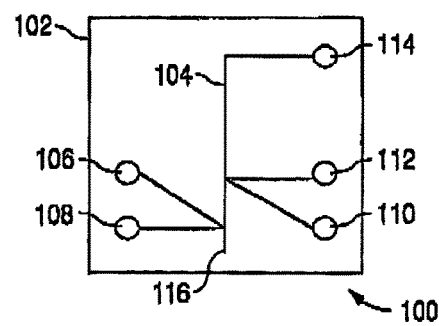
FIG. 1, panels A, B, and C, are a schematic top view, side view, and perspective view of an example microfluidic system comprising the elements of the invention.

Methods and devices in accordance with the invention are capable of rapidly characterizing a variety of biological materials via the generation of molecular melt curves. For example, the molecular melt curve of a double stranded DNA molecule can provide information about the number of base pairs in the molecule, the GC content, and the amount of variation from ideal Watson-Crick base pairing. A molecular melt curve also can be used to indicate the degree of binding between one or more test molecules and a target molecule. "Binding" includes not only, e.g., receptor-ligand interactions, but also, e.g., nucleic acid-nucleic acid hybridization interactions and can include both specific and non-specific interaction. If the test molecules do bind to the target molecule, then their binding can be quantified by the invention. The methods and devices herein are flexible and can be applied to many different types of compounds and molecules. For example, both the target molecule and the test molecules can be any one or more of, e.g., a protein (whether enzymatic or not), an enzyme, a nucleic acid (e.g., DNA and/or RNA, including, single-stranded, double-stranded, or triple-stranded molecules), a ligand, a peptide nucleic acid, a cofactor, a receptor, a substrate, an antibody, an antigen, a polypeptide, monomeric and multimeric proteins (either homomeric or heteromeric), synthetic oligonucleotides, portions of recombinant DNA molecules or chromosomal DNA, portions or pieces of proteins/peptides/receptors/etc. that are capable or having secondary, tertiary, or quaternary structure, etc. The target molecule also optionally interacts with, e.g., co-enzymes, co-factors, lipids, phosphate groups, oligosaccharides, or prosthetic groups.

Briefly, the methods and devices of the invention enable the construction of and comparison of molecular melt curves. Molecular melt curves are alternatively described as "thermal melting curves", "thermal melt curves", "thermal property curves", "thermal denaturation curves" or "thermal profile curves." Accordingly, an analysis involving the generation of molecular melt curve can also be described as a molecular melt analysis, a thermal melting analysis, a thermal melt analysis, a thermal property analysis, a thermal denaturation analysis, or a thermal profile analysis. In such an analysis, a sample of a target molecule, or target molecules, to be tested is flowed into one or a number of microchannels in a microfluidic device. Optionally, the target molecule is then contacted with one or more test molecules that are screened for possible binding capability with the target molecule and/or with an indicator such as a fluorescence indicator dye or molecule. Optional embodiments of the present invention allow for multiple configurations of, e.g., heat application, flow speed, reagent composition, binding conditions, and timing of all the multiple variants involved.

Once the test molecule interacts with the target molecule and/or labeling compound, the present invention sets the reaction conditions, in a controllable manner, to a desired temperature (either continuously over a range of temperatures or non-continuously to discrete temperature points). Selected physical properties of the molecules are measured in the microfluidic device and thermal property curves produced from the measurements. The thermal property curves are based upon, e.g., the temperature induced denaturation or unfolding that occurs when the molecules are subjected to heat. Denaturation can include, e.g., loss of secondary, tertiary, or quaternary structure by means of uncoiling, untwisting, or unfolding, disassociation of nucleic acid strands, etc. When target and test molecules bind to one another, e.g., as with receptor-ligand interactions, the conformation of the target molecule is stabilized and the pattern of the temperature induced denaturation is altered or shifted. Comparison of the thermal property curve derived from heating just the target molecule, with the thermal property curve derived from heating the target molecule and test molecule(s) in combination, allows the determination and quantification of any binding between the target molecule and the test molecule(s). The adaptability of the current invention optionally allows both thermal property curves to be run simultaneously in the microfluidic device, as well as optionally running multiple configurations of the binding assay simultaneously (e.g., with different reaction parameters, such as pH, temperature gradient(s), etc.).

Numerous types of molecules can be assayed by the methods, devices, and systems of the present invention. For example, protein-protein binding reactions can be examined, including, e.g., receptor-ligand, antibody-antigen, and enzyme-substrate interactions. Additionally, interactions between, e.g., amino acid based molecules and nucleic acid based molecules can be examined. Similarly, artificial molecules such as peptide nucleic acids (PNAs) can be monitored, e.g., in interactions of the PNAs with nucleic acids or other molecules. Also, screening for interactions between hydridization probes and nucleic acids, e.g., comprising single nucleotide polymorphisms (SNPs), can be accomplished through use of the current invention. For examples of types of molecular interactions optionally assayed by the invention, see,—e.g., Weber, P. et al., (1994) "Structure-based design of Synthetic Azobenzene Ligands for Streptavidin" *J Am Chem Soc* 16:2717-2724; Brandts, J. et al., (1990) *American Laboratory,* 22:3041+; Gonzalez, M. et al., (1997) "Interaction of Biotin with Streptavidin", *J Biol Chem,* 272(17): 11288-11294; Chavan, A. et al., (1994) "Interaction of nucleotides with acidic fibroblast growth factor (FGF-1) *Biochem,* 33(23):7193-7202; Morton, A. et al., (1995) "Energetic origins of specificity of ligand binding in an interior nonpolar cavity of T4 lysozyme." *Biochem,* 34(27):8564-8575; Kleanthous, C. et al., (1991) "Stabilization of the shikimate pathway enzyme dehydroquinase by covalently bound ligand" *J Biol Chem,* 266(17): 10893-10898; Pilch, D. et al., (1994) "Ligand-induced formation of nucleic acid triple helices." *Proc Natl Acad Sci USA,* 91(20): 9332-9336; and Barcelo, F. et al. (1990) "A scanning calorimetric study of natural DNA and antitumoral anthracycline antibiotic-DNA complexes." *Chem Biol Interact,* 74(3): 315-324.

The actual detection of a change(s) in a physical property of the molecules can be detected in numerous methods depending on the specific molecules and reactions involved. For example, the denaturation of the molecules can be tracked by following fluorescence or emitted light from molecules in the assay. The degree of, or change in, fluorescence is correlational or proportional to the degree of change in conformation of the molecules being assayed. The methods and devices of the invention allow for various methods of exciting the molecules involved in the assay, through use of, e.g., lasers, lights, etc. The fluorescence can be intrinsic to the molecules being assayed, e.g., from tryptophan residues in the molecules, or extrinsic to the molecules being assayed, e.g., from fluorophores added to the assay mixture in the microfluidic device. The change(s) in fluorescence or emitted light can optionally be detected in a number of ways according to the specific needs of the assay desired. For example, a charge-coupled device is utilized as an optional part of the device.

The change in fluorescence of emitted light indicates a change in conformation of the target molecule and from which the thermal property curve is constructed. Displacement or shift of the thermal property curve when the target molecule is in the presence of a test molecule allows detection and quantification of binding between the test molecule and the target molecule(s).

Another optional method of detecting changes in conformation of molecules in the invention is by measurement of dielectric properties. As molecules bind and undergo conformational changes, their dielectric properties change as well. These changes can be quantified and used to determine molecular interaction parameters.

An optional way of detecting changes in conformation of the target molecules being assayed in the current invention is through calorimetric measurement. Changes in heat capacity are measured as the molecules in the assay undergo temperature induced denaturation. As with the fluorescence method, binding between molecules is detected and quantified through comparison of the thermal property curves from assays done with just the target molecule and assays done with the combination of the target molecule and test molecule(s).

Thermal Property Curves

The unfolding, disassociation or denaturing of a target molecule(s) in response to changes in temperature can be useful in many applications, e.g., in determining the stability of a specific protein under specified conditions, or in the identification of a nucleic acid, the detection of SNPs in a nucleic acid, etc. The measurement of the molecular denaturing, disassociation or unfolding of the target molecule is used to construct a thermal property curve. In other applications, variations of basic thermal property curves can be used to test for, e.g., whether a specific ligand or other molecule binds to a target molecule. For example, the binding of a specific ligand to a specific receptor can be investigated by a thermal property curve. See, e.g., Gonzalez, M. et al., (1997) "Interaction of Biotin with Streptavidin" *J Biol Chem,* 272(17): 11288-11294. Additionally, hybridization of specific oligonucleotides to each other can be demonstrated with a thermal property curve. See, e.g., Clegg, R. et al. (1994) "Observing the helical geometry of double-stranded DNA in solution by fluorescence resonance energy transfer." *Proc Natl Acad Sci USA* 90(7):2994-2998.

Stabilization Due to Binding

Thermal property curves are based on the change in conformation of a molecule due to changes in temperature. As stated above, molecules, e.g., proteins and nucleic acids, show unfolding, disassociation or denaturation over a range of temperatures. The measurement of the unfolding, etc. of a given target molecule as a function of temperature generates a thermal property curve for that molecule. Binding of, e.g., ligands (e.g., such as nucleic acids or protein) to the target molecule, can lead to stabilization of the molecule and hence a change in its thermal property curve. See, e.g., Gonzalez, M. et al., (1997) "Interaction of Biotin with Streptavidin" *J Biol Chem,* 272(17): 1.1288-11294; Schellman, J. (1975) *Biopolymers,* 14:999-1018; Barcelo, F. et al., (1990) "A scanning calorimetric study of natural DNA and antitumoral anthracycline antibiotic-DNA complexes." *Chem Biol Interactions,* 74(3):315-324; Schellman, J. (1976) Biopolymers, 15:999-1000; and Brandts, J. et al. (1990) "Study of strong to ultratight protein interactions using differential scanning calorimetry" *Biochem* 29:6927-2940.

In other words, binding of the test molecule to the target molecule, e.g., ligand will cause the target molecule to denature (or disassociate, unfold, etc.) in a different manner than it would without the binding. This property, of course, can be extremely useful in many applications, e.g., determining the relative binding affinities of multiple ligands to a target molecule or the binding abilities of mutant proteins, e.g., as described herein. In the generation of thermal property curves, "$T_m$," denotes the "midpoint temperature" or the temperature at which the denaturation or unfolding reaction is half complete.

In some aspects of the current invention, construction of thermal property curves similar to those discussed above can be used to determine a reference temperature encountered by a solution in a microfluidic channel. More specifically, embodiments of the invention allow a reference temperature of a fluid within a microfluidic channel to be correlated to a value of a physical parameter outside the channel that can be readily measured. For many applications, e.g., PCR and/or construction of thermal property curves to test for, e.g., binding of ligands, etc., precise temperature control is needed within the microfluidic elements, such as channels or chambers, of microfluidic devices. The use of a melting curve generated for known molecules (e.g., streptavidin/biotin-fluorescein, etc.) to monitor and calibrate the temperature within microfluidic elements is of great benefit since, e.g., it allows for determination of temperature through use of simple, inexpensive materials, the process can be substantially irreversible or optionally reversible (see, below), it can be fine-tuned by use of different molecules having different melting temperatures (see, below), and it eliminates the need to place a sensor within the microfluidic device. The physical parameter to which the reference temperature is correlated must be a physical parameter that correlates to the temperature within the channel. For example, the physical parameter could be the temperature at an exterior surface of the microfluidic device adjacent to the microfluidic element, the electric current applied to fluid in the element that joule heats the fluid, or the temperature of a thermal block in thermal contact with the microfluidic element.

In some optional embodiments of the present invention, molecules such as streptavidin and biotin-fluorescein are used to calibrate the temperature in a microfluidic device by determining a reference temperature. Free streptavidin (SA), which has a melting temperature of approximately 74° C., is optionally bound with four molecules (e.g., of biotin-fluorescein, etc.), thus causing the SA to have a very sharp melting temperature of about 108° C. When bound to streptavidin, the fluorescein is substantially quenched (i.e., it does not emit fluorescence). But, when the streptavidin molecule is denatured (i.e., by heat in the microchannel), the biotin-fluorescein conjugate is released and thus fluorescence can be detected. To bind biotin-fluorescein to SA, the SA is optionally incubated in the presence of excess biotin-fluorescein conjugate. After saturation, unbound biotin-fluorescein is removed by, e.g., size filtration. The melting temperature of this SA-biotin-fluorescein complex is determined on, e.g., a heated fluorometer or other comparable detector. The SA-biotin-fluorescein complex is then optionally passed through the microchannels of a device of the current invention (i.e., which have a targeted reference temperature). If the proper fluorescence from the SA-biotin-fluorescein system is detected at a location along the length of the microchannel (or at another convenient location) that is programmed to be at the reference temperature, then the predetermined reference temperature was attained in the channel. If the proper fluorescein fluorescence is not detected, then the proper reference temperature was not achieved in the microchannel. In various embodiments, the temperature is optionally also ramped from a high temperature (e.g., 100° C.) to a low temperature (e.g., 40° C.) while the end-point (or other convenient location) fluorescence is monitored. Additionally a series of probes with different melting temperatures (see, below) could be loaded in sequence into the microchannel. In this way, the temperature calibrations are optionally mapped across a range of temperatures.

Commercial biotin-fluorescein conjugates with different properties are optionally utilized in the above temperature determination/calibration (e-g., biotin-4-fluorescein and fluorescein-biotin). Such conjugates differ primarily by the length of the linker. Additionally, biotin-4-fluorescein binds very rapidly to SA (or optionally to avidin (AV) or neutravidin (NA), (5-4N-(5-(N-(6-(biotinoyl)amino)hexanoyl)amino)pentyl)thioureidyl), while fluorescein (also called fluorescein-biotin) binds very slowly (taking up to ten hours to reach saturation, even when present in excess) due to steric hindrance from the linker. After denaturation (i.e., due to increased temperature) the AV/SA/NA optionally renatures. Use of biotin-4-fluorescein with its fast binding time, thus optionally makes the temperature monitoring/calibration assay reversible (i.e., the assay is optionally repeatable (e.g., at a different temperature range or ramp speed) since the biotin-4-fluorescein can rebind to the SA in a relatively short time period). The use of fluorescein-biotin, however, would make the assay substantially irreversible over a period of at least several hours since the binding time is relatively long.

In optional embodiments the monitoring/calibration method is modified by using, e.g., AV, SA, or NA, each of which has a different melting temperature. Additionally the choice of biotin-4-fluorescein or fluorescein-biotin optionally impacts the melting temperature. Native biotin optionally lends the greatest stability to AV, etc., followed by biotin-4-fluorescein and fluorescein-biotin. Furthermore, in other optional embodiments, a denaturant such as urea or guanidine HCl is added to the temperature determination/calibration. Titration of such denaturant concentrations optionally results in the fine-tuning of the calibration to a desired melting temperature. Any attenuations of the temperature of the denaturation by the denaturant are optionally tested for and taken into account in the calibration.

Example Thermal Property Curves

Figure 3:
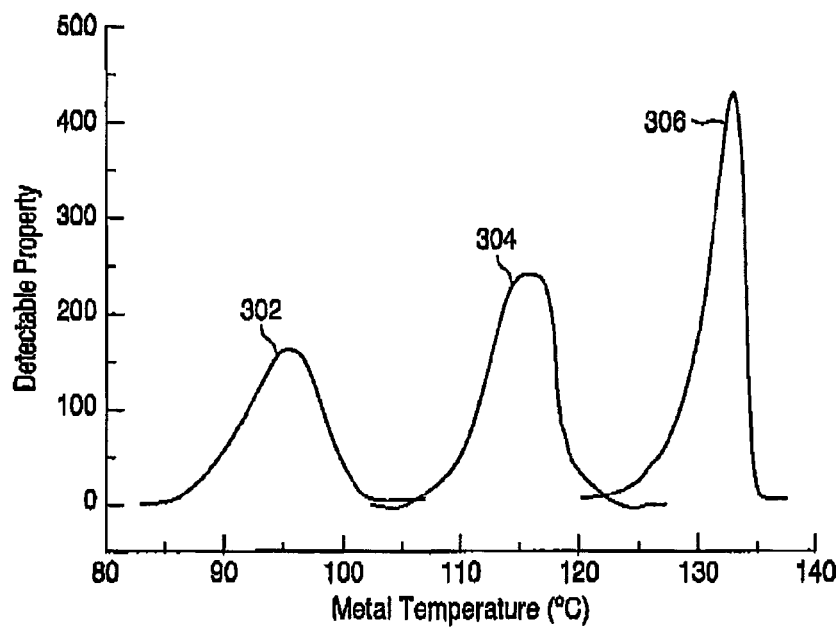
FIG. 3 is a simulated diagram of an example thermal property curve illustrating a shift due to binding of, e.g., a ligand.

FIG. 3, for illustrative purposes only, provides a simulated diagram illustrating shifting of a thermal property curve due to ligand binding. The figure plots a detectable property (e.g., excess heat capacity) as a function of temperature. As explained throughout, other changes are optionally tracked in order to indicate denaturation, e.g., fluorescence of indicator dyes or molecules, intrinsic fluorescence, etc.

Peak 302 represents the thermal property curve for Molecule X where no additional molecule, e.g., ligand, is in contact with molecule X. The $T_m$ of peak 302 centers around 95° C. and represents the melting temperature where at which the denaturation or unfolding of Molecule X is half complete.

Peak 304 represents the thermal property curve for Molecule X plus Molecule Y, which is, e.g., a ligand that binds to Molecule X. The $T_m$ for Molecule X when bound with Molecule Y "shifts" and centers around 115° C.

Peak 306 represents the thermal property curve for Molecule X plus Molecule 2, which is, e.g., an alternate ligand that binds to Molecule X. The $T_m$ for Molecule X when bound with Molecule Z "shifts" and centers around 133° C.

Figure 4A:
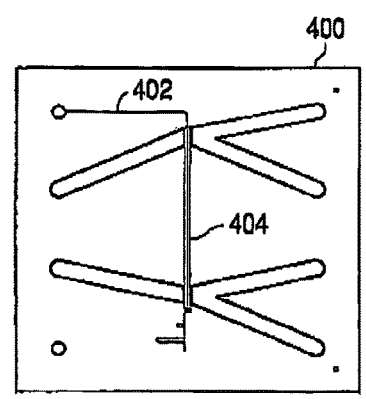
FIG. 4, panels A and B, are schematic examples of microfluidic chips capable of use in construction of thermal property curves.
Figure 5:
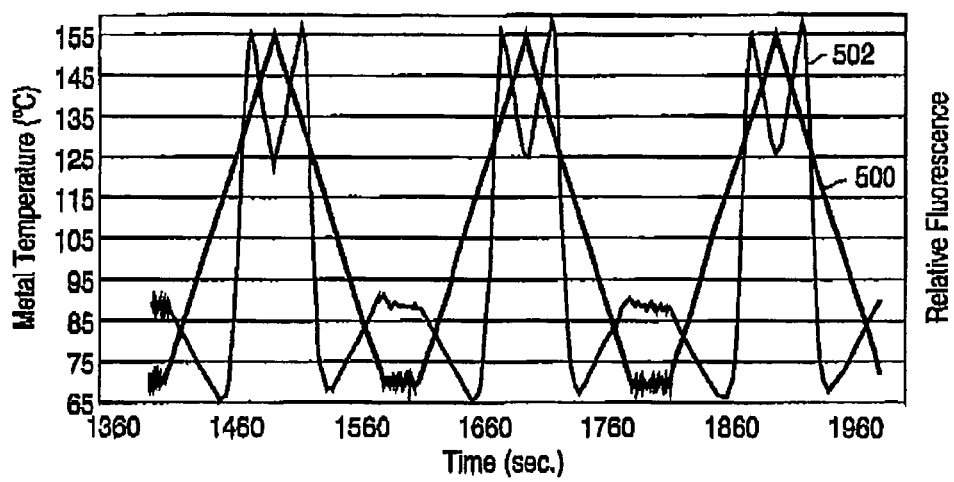
FIG. 5 is a graph generated from the thermal disassociation of a double stranded oligonucleotide, showing emitted fluorescence over a range of temperatures.
Figure 6:
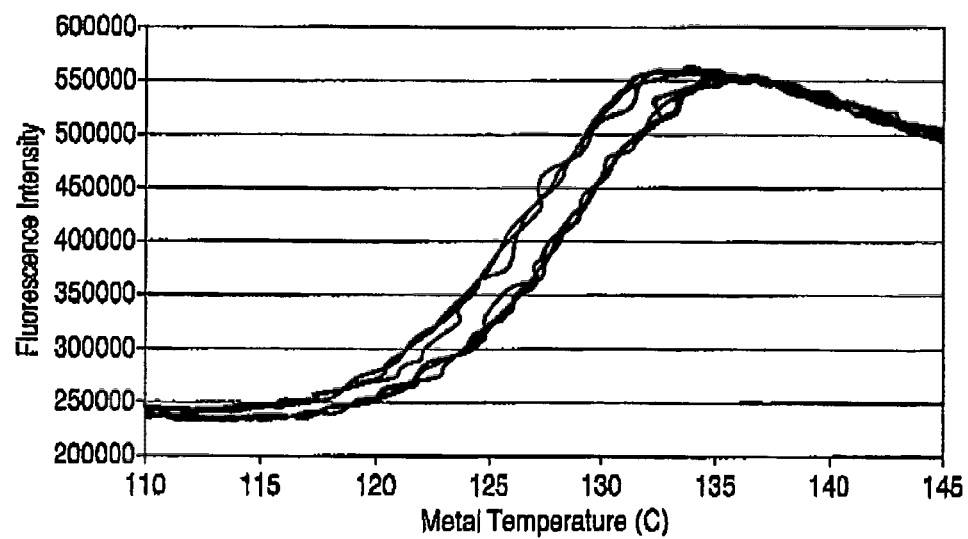
FIG. 6 is a thermal property curve constructed from data generated from the thermal disassociation of a double stranded oligonucleotide.

Another example of the uses of the methods/devices of the current invention is shown in FIGS. 4a, 5 and 6. The tracking of disassociation between the strands of a double stranded DNA oligonucleotide, as illustrated in FIGS. 4a, 5 and 6, is done by measurement of emitted fluorescence over a range of temperatures. As is well known in the art, because of, e.g., their differing compositions, different double stranded nucleic acids (such as the double stranded DNA used in FIGS. 4a, 5 and 6) disassociate at different temperatures. If two associated strands are not perfectly matched, e.g., because one strand contains an SNP, then the disassociation temperature profile (i.e., the thermal property curve) will be different than the curve/profile produced by the melting of two perfectly matched strands.

To produce the graphs shown in FIGS. 5 and 6, a 35-basepair DNA oligonucleotide (double stranded) was designed so that its disassociation over a range of temperature could be followed using FRET (see, below for a discussion of FRET). The oligonucleotide was synthesized by Oligos Etc. Inc. of Bethel, Minn. and had the following sequence:

```
                                                    (SEQ ID NO: 1)
3' GTAGG TTCCT CATCG ACACA GTAGT CCGGG CGGCG 5' - fluorescein (SEQ ID NO: 2)
5' CATCC AAGGA GTAGC TGTGT CATCA GGCCC GCCGC 3' - TAMRA.
```

Of course, similar oligonucleotides are easily available from numerous commercial sources well known to those skilled in the art and can also be readily synthesized by ones skilled in the art. It will be appreciated that methods and devices of the current invention are not constrained to use of particular nucleic acid sequences or lengths. In other words, all conceivable nucleic acid sequenceslcombinations are capable of utilization in the current invention and the above oligonucleotide sequences should not be considered limiting. Thus methods and devices in accordance with the invention could be used for diagnostic applications, e.g., to analyze DNA obtained from a patient sample that has been purified and amplified by PCR.

In this example, fluorescein on one half of the oligonucleotide strand acts as the FRET donor while the TAMRA (6-carboxytetramethylrhodamine) on the other half of the oligonucleotide strand acts as the FRET acceptor (see, below for other possible emitter/acceptor pairs useful for similar measurements). Therefore, when the DNA is in a double-stranded conformation (and hence the fluorescein is in close proximity to the TAMRA), the fluorescence from the fluorescein is transferred to the TAMRA. As the temperature is raised, the two strands separate (again, the specific temperature depending upon, e.g., the specific sequence of the oligonucleotides used), thus separating the fluorescein and TAMRA and thereby allowing a fluorescent emission to be detected from the fluorescein.

The melting curve of the above listed oligonucleotide was monitored in a microfluidic chip, 400, as shown in FIG. 4a. The oligonucleotide was flowed through microchannel 402 at −4 psi. Channel 402 and its contents was heated by passing electric current through resistive heating elements 404, which are 3000 Å thick metal traces, 404 extending alongside channel 402 for approximately 20 mm. The fluorescein moiety was excited with 485 nm wavelength energy and the resulting emitted fluorescence was measured at a wavelength of 520 nm. Such measurement was done through an objective lens positioned at the center of channel 402. The temperature in channel 402 was held at an initial temperature for 30 seconds, then increased at a rate of 1° C./sec for 95 seconds to a second temperature (see, graphs in FIGS. 5 and 6 for temperature ranges). The temperature was then decreased back down to the initial temperature, again at a rate of 1° C./sec for 95 seconds. Such cycling was repeated three times total. The temperature and fluorescence profiles (represented by line 500 and line 502, respectfully) are shown in FIG. 5. The resulting melting curve is shown in FIG. 6. In addition to checking for mismatched nucleic acid strands, such thermal melting curves as are generated by the above example in FIG. 4a, can be utilized to measure/verify the internal temperature of a fluidic material in a microchannel or other similar microelement since the $T_m$ of a known double-stranded nucleic acid can be calculated. In other words, if, e.g., a double stranded DNA oligonucleotide with a known $T_m$ is labeled in a manner similar has a melting curve generated for it within a microfluidic device, then the conditions required to reach a temperature $T_m$ on that microfluidic device can be determined. In other words, $T_m$ can serve as a reference temperature for that microfluidic device.

Figure 4B:
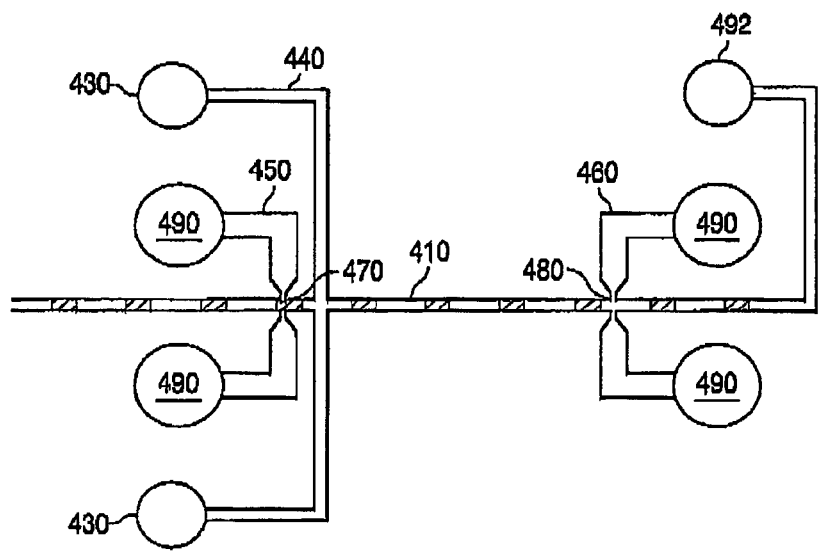

Even though the prior examples demonstrating construction of a thermal property curve for labeled oligonucleotides of known composition was carried out in a microfluidic chip as shown schematically in FIG. 4a, it will be appreciated that such thermal property curves (and indeed, any of the thermal property curves described herein) are optionally carried out in a myriad of different arrangements/configurations of microfluidic chips. For example, similar thermal property curves, or, again, basically any thermal property curve as described herein, is optionally done in a chip such as that shown in FIG. 4b. As shown in FIG. 4b, molecules are optionally flowed through main channel 410. Channel 410 is in fluid communication with two large electrical access channels, 450 and 460, at intersections 470 and 480. A traverse channel, 440, for introducing such things as, e.g., specific dyes, markers, etc. (e.g., dyes which only bind to hydrophobic amino acid regions in proteins, etc.), is in fluid communication with the main channel 410. The electrical access channels 450 and 460 are in fluid communication with filled reservoirs 490, and flow an electrical current into the main channel between the intersections 470 and 480 (see, below for a description of heating through use of an electric current in a microchannel, joule heating). The electrical resistance of the electrical access channels 450 and 460 is less than the electrical resistance of the main channel 410. The heating region of the main channel is defined by intersections 470 and 480, and is optionally of varying lengths and depths in different embodiments depending upon the specific heating/flow needs of the assays in question. The molecules to be assayed (e.g., a protein and a putative binding molecule to that protein) are introduced into the main channel via a sample loading source. Upon entering the heating region in the main channel (i.e., between 470 and 480), each molecule and putative binder undergoes heating (e.g., in steps or continuously) as it travels through the region. Also in this region, a detection system appropriate to the assay conditions (e.g., optical detectors to measure fluorescence, see, below) is positioned to measure any physical properties of the molecules (e.g., fluorescence) over the temperature range and convey such readings to a computer in order to construct thermal property curves (optionally including control or calibration curves wherein the putative binding molecules are not added to the, e.g., protein molecule to be tested in the main channel). Other examples of microfluidic devices and integrated systems in accordance with the invention are provided in the "Example Integrated Systems" section below.

Detectable Properties Used to Construct Thermal Property Curves

In constructing a thermal property curve, a physical property of the molecule in question must be measured in order to determine the denaturation/unfolding of the molecule. The change in this physical property is measured as a function of changing temperature and is proportional/correlative to the change in conformation of the molecule. For example, a change in calorimetric analysis, heat capacity, can be measured to. indicate the temperature induced denaturation of molecules, see, e.g., Weber, P. et al., (1994) "Structure-based design of Synthetic Azobenzene Ligands for Streptavidin" *Jam Chem Soc* 16:27 17-2724. Additional physical properties which can be measured to indicate a change in molecular folding/conformation include, e.g., various spectral phenomena, such as presence of fluorescence or emitted light, changes in fluorescence or emitted light, or changes in polarization of fluorescence or emitted light. These properties can be measured over a range of temperatures and correlated to changes in the unfolding/denaturation of target molecule(s) under examination in the microfluidic device.

Calorimetry—

One embodiment of the present invention uses calorimetry to measure changes in thermodynamic parameters as the target molecule is subjected to changes in temperature. For example, differential scanning calorimetry (DSC) is optionally used to measure the relative stability of molecules. Using DSC in the current invention, a sample containing the target molecule is heated over a range of temperatures in the microfluidic device. At some point during the heating process the target molecule undergoes a physical or chemical change, e.g., denaturation, that either absorbs or releases heat. The thermal change(s) during the process is then plotted as a function of temperature with the area under the curve representing the total heat or enthalpy change (AH) for the entire process. Those skilled in the art can use the resulting plots to determine, e.g., heat capacity change (ΔCp), the $T_m$ (or midpoint temperature where the denaturation or unfolding reaction is half complete), or the like. See, e.g., Gonzalez, M. et al., (1997) "Interaction of Biotin with Streptavidin", *J Biol Chem*, 272(17): 11288-1 1294.

The above procedure is optionally repeated with the addition of a test molecule (or test molecules) that might possible binds to the target molecule, e-g., a ligand. The thermal property curve generated by heating the target molecule and its putative binder molecule(s) is then compared with the thermal property curve generated by heating the target molecule by itself. Comparison of the two thermal property curves can disclose, e.g., whether the test molecule actually binds to the target molecule. If the molecules do bind to each other then the thermal property curve of the target molecule assayed in the presence of the test molecule will be 'shifted' in comparison to the thermal property curve of the target molecule by itself. This shift in the thermal property curves is due to a binding-dependent change in the thermal denaturation of the target molecule. Binding stabilizes the target molecule. See, e.g., Gonzalez, M. et al., (1997) "Interaction of Biotin with Streptavidin", *J Biol Chem*, 272(17):11288-11294; and Barcelo, F. et al. (1990) "A scanning calorimetric study of natural DNA and antitumoral anthracycline antibiotic-DNA complexes." *Chem Biol Interact*, 74(3):315-324.

Current—

Another embodiment of the invention uses the measurement of applied current to track the denaturation/unfolding of a target molecule as a function of temperature. Joule heating can be applied in "clamp" mode. The amount of current needed to maintain a certain temperature or temperatures is measured as the molecules (i.e., both individually and in combination) under examination are cycled through the temperatures in the device.

Fluorescence—

Another embodiment of the present invention uses spectroscopy to measure changes in fluorescence or light to track the denaturation/unfolding of the target molecule as the target molecule is subjected to changes in temperature. Spectrometry, e.g., via fluorescence, is a useful method of detecting thermally induced denaturation/unfolding of molecules. Many different methods involving fluorescence are available for detecting denaturation of molecules (e.g., intrinsic fluorescence, numerous fluorescence indicator dyes or molecules, fluorescence polarization, fluorescence resonance emission transfer, etc.) and are optional embodiments of the present invention. These methods can take advantage of either internal fluorescent properties of target molecules or external fluorescence, i.e. the fluorescence of additional indicator molecules involved in the analysis.

Intrinsic Fluorescence—

An optional method of measuring the degree of denaturation/unfolding of the target molecule (when the target molecule is amino acid based) is through monitoring of intrinsic fluorescence of, e.g., tryptophan residues. Other aromatic amino acid residues, in addition to tryptophan, exhibit intrinsic fluorescence and optionally are utilized in the invention. As the target molecule undergoes unfolding due to increases in temperature, various tryptophan or other molecules which were previously nestled in the interior of the protein structure can become exposed to solvent surrounding the molecule(s). This change in exposure of the, e.g., tryptophan residues leads to a corresponding change in the fluorescence of the target molecule. The quantum yield of the emission either decreases or increases depending on the sequence and conformation of the target molecule. Upon unfolding of the target molecule, there is usually a red shift in the intrinsic emission of the molecule, which optionally can also be used to detect conformational changes. See, e.g., Ropson, I. et al. (1997) "Fluorescence spectral changes during the folding of intestinal fatty acid binding protein" *Biochem,* 36(38):8594-8601. The changes in intrinsic fluorescence observed from this method are measured as a function of temperature and used to construct thermal property curves. As described above, binding of a test molecule(s) to the target molecule shifts the thermal property curve and is used to determine and quantify/qualify the binding event.

Fluorescence Indicator Dyes and Molecules—

Another method of measuring the degree of denaturation/unfolding of the target molecule is through monitoring of the fluorescence of indicator dyes or molecules added to the microfluidic device along with the target molecule and any test molecules of interest. "Fluorescence indicator dye" or "fluorescence indicator molecule" refers to a fluorescent molecule or compound (i.e., a fluorophore) which can bind to a target molecule either once the target molecule is unfolded or denatured or before the target molecule undergoes conformational change by, e.g., denaturing and which emits fluorescent energy or light after it is excited by, e-g., light of a specified wavelength. "Fluorescence indicator dye" and "fluorescence indicator molecule" includes all fluorophores.

For example, fluorescence dyes which bind specifically to certain regions on molecules are optionally used in the present microfluidic device to monitor the molecular unfolding/denaturation of the target molecule due to temperature. One example of a group of such fluorescence dyes consists of dyes that bind specifically to hydrophobic areas of molecules. An illustrative, but not limiting, example of a dye in that group is 1-anilino-8-naphthalene sulfonate (ANS). ANS has a low fluorescence in polar environments, but when it binds to apolar regions, e.g., such as those found in interior regions of natively folded proteins, its fluorescence yield is greatly enhanced. As target molecules are denatured, e.g., as happens with increasing temperature in the microfluidic device, they become denatured thereby allowing solvent, e.g., water, to reach and quench the fluorescence of the ANS. Alternatively, ANS can be used to monitor temperature induced conformational changes in other ways as well depending on the specific molecules/reactions/etc. being studied in the microfluidic device of the invention (e.g., the path of denaturation of a protein can create hydrophobic regions to which ANS can bind and fluoresce; alternatively, denaturation allows creation of hydrophobic protein globules to which ANS can bind; ANS fluorescence can be monitored as ANS competes with ligands for binding sites on proteins, etc.). See, e.g., Schonbrunn, E. et al. (2000) "Structural basis for the interaction of the fluorescence probe 8-anilino-1-naphthalene sulfonate (ANS) with the antibiotic target MurA" *Proc Natl Acad Sci USA* 97(12):6345-6349; and Ory, J. et al. (1999) "Studies of the Ligand Binding Reaction of Adipocyte Lipid Binding Protein Using the Fluorescent Probe 1,8-Anilinonaphthalene-8-Sulfonate-"*Biophys* 77: 1107-1116. Various other hydrophobic fluorescence dyes, etc. are well known to those in the art as are fluorescence dyes which bind to other specific classes of areas on target molecules to be assayed in the microfluidic device and which are optionally embodied in the current invention.

Another optional dye type used in the current microfluidic device is one that intercalates within strands of nucleic acids. The classic example of such type of dye is ethidium bromide. An example of use of ethidium bromide for binding assays includes, e.g., monitoring for a decrease in fluorescence emission from ethidium bromide due to binding of test molecules to nucleic acid target molecules (ethidium bromide displacement assay). See, e.g., Lee, M. et al., (1993) "In vitro cytotoxicity of GC sequence directed alkylating agents related to distamycin" *J Med Chem* 36(7):863-870. The use of nucleic acid intercalating agents in measurement of denaturation is well known to those in the art. See, e.g., Haugland (1996) Handbook of Fluorescent Probes and Research Chemicals Published by Molecular Probes, Inc., Eugene, Oreg.

Dyes that bind to nucleic acids by mechanisms other than intercalation can also be employed in embodiments of the invention. For example, dyes that bind the minor groove of double stranded DNA can be used to monitor the molecular unfolding/denaturation of the target molecule due to temperature. Examples of suitable minor groove binding dyes are the SYBR Green family of dyes sold by Molecular Probes, Inc. of Eugene Oreg. See, e.g., Haugland (1996) Handbook of Fluorescent Probes and Research Chemicals Published by Molecular Probes, Inc., Eugene, Oreg. SYBR Green dyes will bind to any double stranded DNA molecule. When a SYBR Green dye binds to double stranded DNA, the intensity of the fluorescent emissions increases. As more double stranded DNA are denatured due to increasing temperature, the SYBR Green dye signal will decrease.

Fluorescence Polarization—

Other embodiments of the invention utilize fluorescence polarization. Fluorescence polarization (FP) provides a useful method to detect hybridization formation between molecules of interest. This method is especially applicable to hybridization detection between nucleic acids, e.g., to monitor single nucleotide polymorphisms (SNPs).

Generally, FP operates by monitoring the speed of rotation of fluorescent labels, such as fluorescent dyes, e.g., before, during and/or after binding events between molecules that comprise the test and target molecules. In short, binding of a test molecule to the target molecule ordinarily results in a decrease in the speed of rotation of a bound label on one of the molecules, resulting in a change in FP.

For example, when a fluorescent molecule is excited with a polarized light source, the molecule will emit fluorescent light in a fixed plane, e.g., the emitted light is also polarized, provided that the molecule is fixed in space. However, because the molecule is typically rotating and tumbling in space, the plane in which the fluoresced light is emitted varies with the rotation of the molecule (also termed the rotational diffusion of the molecule). Restated, the emitted fluorescence is generally depolarized. The faster the molecule rotates in solution, the more depolarized it is. Conversely, the slower the molecule rotates in solution, the less depolarized, or the more polarized it is. The polarization value (P) for a given molecule is proportional to the molecule's "rotational correlation time," or the amount of time it takes the molecule to rotate through an angle of approximately 68.5°. The smaller the rotational correlation time, the faster the molecule rotates, and the less polarization will be observed. The larger the rotational correlation time, the slower the molecule rotates, and the more polarization will be observed. Rotational relaxation time is related to viscosity (q) absolute temperature (T), molar volume (V), and the gas constant (R). The rotational correlation time is generally calculated according to the following formula: Rotational Correlation Time=3 $\eta$V/RT. As can be seen from the above equation, if temperature and viscosity are maintained constant, then the rotational relaxation time, and therefore, the polarization value, is directly related to the molecular volume. Accordingly, the larger the molecule, the higher its fluorescent polarization value, and conversely, the smaller the molecule, the smaller its fluorescent polarization value.

In the performance of fluorescent binding assays in the current invention, a typically small, fluorescently labeled molecule, e.g., a ligand, antigen, etc., having a relatively fast rotational correlation time, is used to bind to a much larger molecule, e-g., a receptor protein, antibody, etc., which has a much slower rotational correlation time. The binding of the small labeled molecule to the larger molecule significantly increases the rotational correlation time (decreases the amount of rotation) of the labeled species, namely the labeled complex over that of the free unbound labeled molecule. This has a corresponding effect on the level of polarization that is detectable. Specifically, the labeled complex presents much higher fluorescence polarization than the unbound, labeled molecule.

In addition to Nikiforov and Jeong "Detection of Hybrid Formation between Peptide Nucleic Acids and DNA by Fluorescence Polarization in the Presence of Polylysine" (1999) *Analytical Biochemistry* 275:248-253, other references that discuss fluorescence polarization and/or its use in molecular biology include Perrin "Polarization de la lumiere de fluorescence. Vie moyenne de molecules dans l'etat excite" (1926) *J Phys Radium* 7:390; Weber (1953) "Rotational Brownian motion and polarization of the fluorescence of solutions" *Adv Protein Chem* 8:415; Weber (1956) *J Opt Soc Am* 46:962; Dandliker and Feigen (1961), "Quantification of the antigen-antibody reaction by the polarization of fluorescence" *Biochem Biophys Res Commun* 5:299; Dandliker and de Saussure (1970) (Review Article) "Fluorescence polarization in immunochemistry" *Immunochemistry* 7:799; Dandliker W. B., et al. (1973), "Fluorescence polarization immunoassay. Theory and experimental method" *Immunochemistry* 10:219; Levison S. A., et al. (1976), "Fluorescence polarization measurement of the hormone-binding site interaction" *Endocrinology* 99:1129; Jiskoot et all. (1991), "Preparation and application of a fluorescein-labeled peptide for determining the affinity constant of a monoclonal antibody-hapten complex by fluorescence polarization" *Anal Biochem* 196:421; Wei and Herron (1993), "Use of synthetic peptides as tracer antigens in fluorescence polarization immunoassays of high molecular weight analytes" *Anal Chem* 65:3372; Devlin et al. (1993), "Homogeneous detection of nucleic acids by transient-state polarized fluorescence" *Clin Chem* 39: 1939; Murakami et al. (1991). "Fluorescent-labeled oligonucleotide probes detection of hybrid formation in solution by fluorescence polarization spectroscopy" *Nuc Acids Res* 19:4097. Checovich et al. (1995), "Fluorescence polarization—a new tool for cell and molecular biology" (product review), Nature 375:354-256; Kurnke et al. (1995), "Hybridization of fluorescein-labeled DNA oligomers detected by fluorescence anisotropy with protein binding enhancement" *Anal Chem* 67(21):3945-3951; and Walker, J. et al. (1996), "Strand displacement amplification (SDA) and transient-state fluorescence polarization detection of *mycobacterium tuberculosis* DNA" *Clinical Chemistry* 42(1):9-13.

Fluorescence Resonance Energy Transfer—

Yet another optional embodiment of the invention uses fluorescence resonance energy transfer (FRET) to track the conformational changes of the target molecule (and interactions with test molecules which can bind with the target molecule) as a function of temperature. FRET relies on a distance-dependent transfer of energy from a donor fluorophore to an acceptor fluorophore. If an acceptor fluorophore is in close proximity to an excited donor fluorophore then the excitation of the donor fluorophore can be transferred to the acceptor fluorophore. This causes a concomitant reduction in the intensity of the donor fluorophore and an increase in the emission intensity of the acceptor fluorophore. Since the efficiency of the excitation transfer depends, inter alia, on the distance between the two fluorophores, the technique can be used to measure extremely small distances such as would occur when detecting changes in conformation. This technique is particularly suited for measurement of binding reactions, protein-protein interactions, e.g., such as a protein of interest binding to an antibody, and other biological events altering the proximity of two labeled molecules. Many appropriate interactive labels are known. For example, fluorescent labels, dyes, enzymatic labels, and antibody labels are all appropriate. Examples of interactive fluorescent label pairs include terbium chelate and TRITC (tetrarhodamine isothiocyanate), europium cryptate and Allophycocyanin, DABCYL and EDANS and many others known to those of skill (e.g., donor fluorophores such as carboxyfluorescein, iodoacetamidofluorescein, and fluorescein isothiocyanate and acceptor fluorophores such as iodoacetamidoeosin and tetramethylrhodamine). Similarly, two colorimetric labels can result in combinations which yield a third color, e.g., a blue emission in proximity to a yellow emission provides an observed green emission. With regard to fluorescent pairs, there are a number of fluorophores which are known to quench one another. Fluorescence quenching is a bimolecular process that reduces the fluorescence quantum yield, typically without changing the fluorescence emission spectrum. Quenching can result from transient excited state interactions, (collisional quenching) or, e.g., from the formation of non-fluorescent ground state species. Self quenching is the quenching of one fluorophore by another; it tends to occur when high concentrations, labeling densities, or proximity of labels occurs. FRET is a distance dependent excited state interaction in which emission of one fluorophore is coupled to the excitation of another that is in proximity (close enough for an observable change in emissions to occur). Some excited fluorophores interact to form excimers, which are excited state dimers that exhibit altered emission spectra (e.g., phospholipid analogs with pyrene sn-2 acyl chains). See, e.g., Haugland (1996) Handbook of Fluorescent Probes and Research Chemicals Published by Molecular Probes, Inc., Eugene, Oreg. e.g., at chapter 13; and Selvin, P. (2000) "The renaissance of fluorescence resonance energy transfer" *Nat Struct Biol* 7(9):730-734.

Molecular Beacons—

Other optional embodiments of the invention use molecular beacons in following the conformation changes of target molecules/test molecules as a function of temperature. Molecular beacons are probes (i.e., test molecules in terms of the present invention) that can be used to report the presence of specific nucleic acids. They are especially useful in situations where it is either undesirable or not possible to isolate the nucleic acid hybrids being assayed.

Structurally, molecular beacons are hairpin-shaped nucleic acid molecules having a center 'loop' section of a specific nucleic acid sequence flanked by two complementary end regions (annealed together), one of which has a fluorescence moiety and the other a quencher moiety. The loop region is complementary to a target or specific nucleic acid sequence. When the molecular beacon is not in the presence of its proper target molecule and is in its hairpin conformation, the fluorescence moiety and quencher moiety are in close enough proximity that the fluorescence is quenched and the energy is emitted as heat. However, when the molecular beacon encounters its proper target molecule it changes conformation so that its internal loop region binds to the target nucleic acid sequence. This forces the fluorescence moiety to move away from the quencher moiety, which leads to a restoration of fluorescence. Through use of different fluorophores, molecular beacons can be made in a variety of different colors. DABCYL (a non-fluorescent chromophore) usually serves as the universal quencher in molecular beacons. Molecular beacons can be very specific and thus be used to detect, e.g., single nucleotide differences between molecules in the present invention. See, e.g., Tyagi, S. et al. (1996) "Molecular beacons: probes that fluoresce upon hybridization" *Nut Biotech* 14:303-308; and Tyagi, S. et al. (1998) "Multicolor molecular beacons for allele discrimination" *Nut Biotech* 16:49-53.

Circular Dichroism—

Another optional embodiment of the invention uses circular dichroism (CD) to follow the conformational changes of the target molecules/test molecules as a function of temperature. CD is a type of light absorption spectroscopy which measures the difference in absorbance by a molecule between right-circularly polarized light and left-circularly polarized light. CD is quite sensitive to the structure of polypeptides and proteins. For reviews of the application and technique of CD, see, e.g., Woody, R. (1985) "Circular Dichroism of Peptides" in The Peptides 7:14-114, Academic Press; Johnson, W. (1990) "Protein Secondary Structure and Circular Dichroism: A Practical Guide" *Proteins* 7:205-214. In order to construct molecular melt curves, the present invention optionally uses CD to follow the conformational changes in the target and test molecules caused by changes in temperature.

Dielectric Properties

Optional embodiments of the invention include the use of measurement of dielectric properties to detect and/or track conformational changes of molecules (e.g., those occurring due to interactions between molecules as in, e.g., ligand-receptor binding).

One non-limiting optional arrangement used to measure changes in dielectric properties consists of a target molecule bound to a solid substrate. A signal is then conducted through the bound target molecule (e.g., a certain wavelength of electromagnetic energy) and the unique signal response is then measured. The signal response is modulated by the unique dielectric properties of the bound target molecule. If a test molecule interacts with the bound target molecule then the unique signal response is altered. This alteration in the signal response can be used to determine the affinity and specificity of the test molecule for the target molecule.

Additionally, this method can distinguish between binding of a test molecule at, e.g., an allosteric site on a target molecule and the binding of a test molecule at a characterized interaction site on the target molecule. In other words, non-specific binding produces a distinctly different "signature" than does specific binding. For examples and further details of this detection regime, see, e.g., Smith et al. WO 99/39190, Hefti et al. WO 00145170, and Hefti, J. et al. "Sensitive detection method of dielectric dispersions in aqueous-based, surface-bound macromolecular structures using microwave spectroscopy" *Applied Phys Letters*, 75(12): 1802-1 804.

UV Absorbance

Optional embodiments of the invention include the use of measurement of UV Absorbance to detect and/or track denaturation of nucleic acid molecules, and/or to quantify the total amount of nucleic acid. UV can be employed to measure the extent of denaturation because the UV absorbance value of single stranded nucleic acid molecules is greater than the absorbance value of double stranded nucleic acid molecules.

Integrated Systems, Methods and Microfluidic Devices of the Invention

In addition to the actual detection of conformational changes and construction of thermal property curves, the microfluidic devices of the invention also include numerous optional variant embodiments for, e.g., fluid transport, temperature control, fluorescence detection and heating.

The term "microfluidic device" refers to a device having fluidic channels or chambers that are generally fabricated at the micron to sub-micron scale, e.g., the channel or chamber typically having at least one cross-sectional dimension in the range of less than about 1 mm. The channels in a microfluidic device are sometimes referred to as "microfluidic channels". Microfluidic channels are typically closed channels within the interior of a microfluidic device. In many microfluidic devices, the channels are formed by fabricating grooves on the surface of a first planar substrate, and then enclosing those groove by attaching a second planar substrate to that surface. An integrated system, or microfluidic system, interfaces with the microfluidic device. In many microfluidic systems the microfluidic device is a removable component, like a cartridge. Microfluidic devices in accordance with the current invention can be fabricated from materials that are compatible with the conditions present in the specific experiments, etc. under examination. Such conditions include, but are not limited to, pH, temperature, ionic concentration, pressure, and application of electrical fields. For example, as described throughout, the systems mentioned can utilize temperature control to provide thermal melting curves according to the methods herein. Accordingly, materials can be selected to provide particular properties at any selected temperature. The materials of the device are also chosen for their inertness to components of the experiments to be carried out in the device. Such materials include, but are not limited to, glass, quartz, silicon, and polymeric substrates, e.g., plastics, depending on the intended application.

Figure 7:
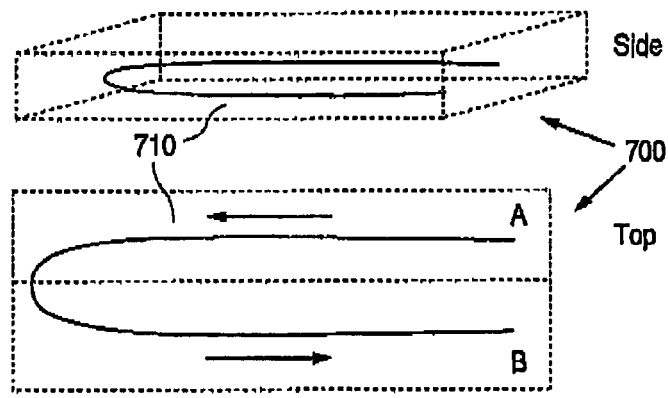
FIG. 7 is a schematic depiction of a microfluidic device in accordance with the invention.

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquotting, and the like. A schematic diagram of a microfluidic device that performs an operation upstream of an operation in accordance with the invention that generates a melt curve is shown in FIG. 7. The microfluidic device 700 comprises a microfluidic channel 710. The general direction of flow through the channel 710 is indicated by the arrows in the top view of the device. An upstream operation is performed in region A of the device, while a melt curve is generated in downstream region B. One particularly advantageous application of the scheme shown in FIG. 7 is to perform sample purification and/or nucleic acid amplification to isolate and amplify a nucleic acid molecule of interest in region A, while downstream in region B the isolated and/or purified nucleic acid molecule of interest is characterized by means of a melt curve in region B. Examples of amplification reactions that could be employed include PCR and LCR. In order to carry out the amplification in upstream region A, the appropriate amplification reagents must be mixed with the nucleic acid of interest within that region. For example, if the nucleic acid molecule is a DNA molecule, and the amplification reaction is PCR, the amplification reagents would include the appropriate primers, a thermostable polymerase, and nucleotides. Downstream operations optionally include similar operations, including, e.g., separation of sample components, labeling of components, assays and detection operations, electrokinetic or pressure-based injection of components or the like.

Integrated microfluidic systems in accordance with the present invention can include other features, such as a fluid transport system that directs fluid and possibly particle movement within the microchannels. The fluid transport system could conceivably employ any fluid movement mechanism known in the art (e.g., fluid pressure sources for modulating fluid pressure in the microchannels, electrokinetic controllers for modulating voltage or current in the microchannels, gravity flow modulators, magnetic control elements for modulating a magnetic field within the microchannels, or combinations thereof).

The microfluidic devices of the invention can also include fluid manipulation elements such as a parallel stream fluidic converter, i.e., a converter that facilitates conversion of at least one serial stream of reagents into parallel streams of reagents for parallel delivery of reagents to a reaction site or reaction sites within the device. For example, the systems herein optionally include a valve manifold and a plurality of solenoid valves to control flow switching between channels and/or to control pressure/vacuum levels in the microchannels, e.g., analysis or incubation channels. Another example of a fluid manipulation element includes, e-g., a capillary optionally used to sip a sample or samples from a microtiter plate and to deliver it to one of a plurality of channels, e.g., parallel reaction or assay channels. Additionally, molecules, etc. are optionally loaded into one or more channels of a microfluidic device through one pipettor capillary fluidly coupled to each of one or more channels and to a sample or particle source, such as a microwell plate.

In the present invention, materials such as cells, proteins, antibodies, enzymes, substrates, buffers, or the like are optionally monitored and/or detected, e.g., so that the presence of a component of interest can be detected, an activity of a compound can be determined, or an effect of a modulator on, e.g., an enzyme's activity, can be measured. Depending on the detected signal measurements, decisions are optionally made regarding subsequent fluidic operations, e.g., whether to assay a particular component in detail to determine, e.g., kinetic information, e.g., based upon analysis of thermal melting curves.

The systems described herein optionally include microfluidic devices, as described above, in conjunction with additional instrumentation for controlling fluid transport, flow rate and direction within the devices, detection instrumentation for detecting or sensing results of the operations performed by the system, processors, e-g., computers, for instructing the controlling instrumentation in accordance with preprogrammed instructions, receiving data from the detection instrumentation, and for analyzing, storing and interpreting the data, and providing the data and interpretations in a readily accessible reporting format.

Temperature Control

Embodiments of the present invention use temperature control to effectuate molecular melting or denaturation for the melting curve assays. Integrated systems in accordance with the invention can also control temperatures to control reaction parameters, e.g., in thermocycling reactions (e.g., PCR, LCR), or to control reagent properties. In general, and in embodiments of the invention, a variety of heating methods can be used to provide a controlled temperature in miniaturized fluidic systems. Such heating methods include both joule and non-joule heating. Non-joule heating methods can be internal to the microfluidic device, i.e., integrated into the structure of the microfluidic device, or external, i.e., separate from the microfluidic device, but part of the microfluidic system. Non-joule heating can be implemented by photon beams, conductive or convective heating and cooling via a fluid (e.g. passing a liquid through channels in the device, or contacting one or more external surfaces of the device with a gas or liquid), lasers, electromagnetic fields, electron beams, thermoelectric heaters, furnaces, resistive thin films, resistive heating coils, peltier heaters, and thermoelectric heaters or coolers. Many of those non-joule heating methods can be used in conjunction with a thermal block, which is a block of thermally conducting material in thermal contact with an external surface of the microfluidic device that transfers thermal energy to or from the microfluidic device by conduction. The block of thermally conducting material is in "thermal contact" with the microfluidic channels within the interior of the microfluidic device in that temperature changes in the block will cause temperature changes in the microfluidic channels. The temperature of the thermal block can be manipulated using one or more of the previously listed non-joule heating methods. For example, the temperature of the thermal block could be manipulated by controlling the current passing through resistive heaters in thermal contact with the thermal block, or by controlling the current passing through a peltier device. An controller in the system interfacing with the microfluidic device, or within the microfluidic device itself can be used to regulate the temperature involved. These examples are not limiting and numerous other energy sources can be utilized to raise the fluid temperature in the microfluidic device.

Non-joule heating units can attach directly to an external portion of a chip of the microfluidic device. Alternatively, non-joule heating units can be integrated into the structure of the microfluidic device. In either case, the non-joule heating is optionally applied to only selected portions of chips in microfluidic devices or optionally heats the entire chip of the microfluidic device and provides a uniform temperature distribution throughout the chip.

A variety of methods can be used to lower fluid temperature in the microfluidic system, through use of energy sinks. The energy sink can be a thermal sink or a chemical sink and can be flood, time-varying, spatially varying, or continuous. The thermal sink can include, among others, a fluid jet, a liquid jet, a gas jet, a cryogenic fluid, a super-cooled liquid, a thermoelectric cooling means, e.g., peltier device or an electromagnetic field. An energy sink can be used to cool a region of a microfluidic device that is also being heated using any joule or non-joule heating method. For example, an energy sink in the form of liquid cooling can be applied to the back side of microfluidic device 100 in FIG. 10 to lower the temperature of the heated region 130, while the metal traces 150 can be used to raise the temperature of the heated region 130. The use of an energy sink in conjunction with a joule or non-joule heating method enables the microfluidic device to change temperatures more rapidly during thermal cycling.

Most of the non-joule heating methods commonly used provide thermal energy to the microfluidic device do not directly provide that energy to the channels in the device. For example, many of the non-joule heating methods listed above deliver heat to an external surface of the microfluidic device, so in those methods the heat must be conducted through the body of the microfluidic device before it reaches the fluid in the channels. For example, in embodiments employing a thermal block, effecting a temperature change in the fluid contained within a microfluidic channel requires that heat be transferred to or from the block through the interface between the block and the microfluidic device, through the body of the microfluidic device, and through the interior surfaces of the channel. The need to conduct heat through the various interfaces and the body of the microfluidic device can create thermal inertia, which introduces a delay between the time the thermal block is heated or cooled and the time that heating or cooling affects the temperature within a microchannel in the device. Furthermore, since almost all non-joule heating methods to not heat the entire body of the microfluidic device uniformly, e.g. heat may be applied to only one surface of the device, or one surface of the device may be heated while another surface of the device is cooled, it is quite common to have a temperature variations within the body of the microfluidic device. In other words, the temperature in the channels of a microfluidic device may be different than the temperature on one or more of the external surfaces of the device.

Figure 8:
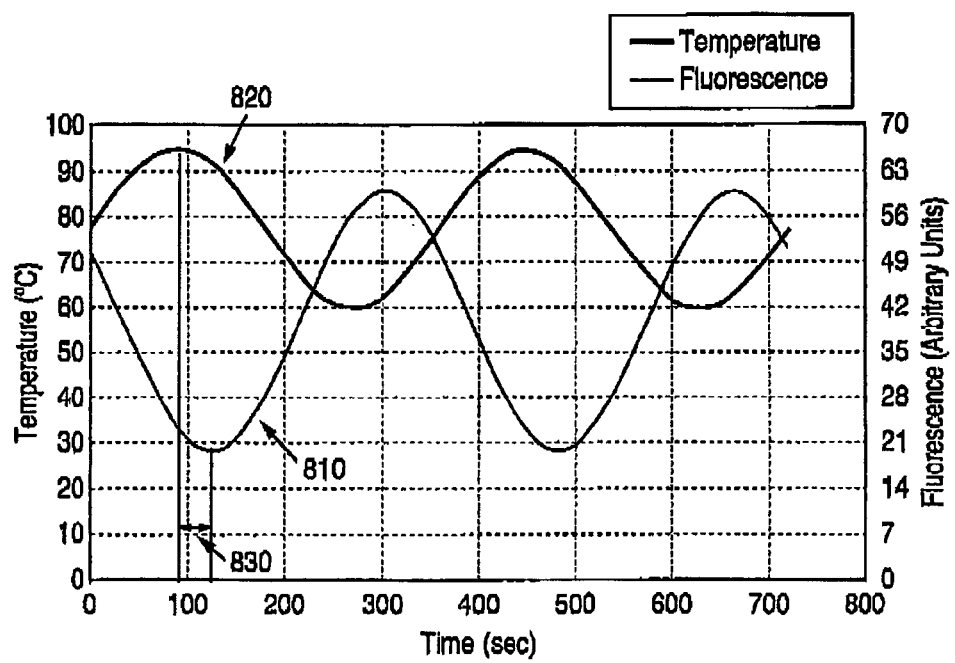
FIG. 8 shows the variation in time of a measured temperature and of a fluorescent signal.

The delay in temperature response in the channels due to thermal inertia, and the offset between the surface temperature and the channel temperature can make extremely precise temperature control of the fluids within the channels of the device problematic because it is typically quite difficult to place a temperature measuring device within a microchannel. The previously described methods for determining a reference temperature within a microfluidic channel can be used to quantify the temperature offset. The delay in response time can be quantified, and thus compensated for, in a number of ways. One method of quantifying the delay is shown in FIG. 8. Since the amount of fluorescence produced by most fluorescent materials varies with temperature, the relative amount of fluorescence in a channel can be an indication of the relative temperature in the channel. As shown in FIG. 8, the temperature 820 of an external surface of a microfluidic device can be varied in a characteristic pattern by directly heating and cooling that surface. The characteristic pattern in FIG. 8 is a sine wave. The pattern of temperature variations applied to a surface of the device will produce a similar pattern of temperature variations in the channels within the device that are in thermal contact with that surface. Since the amount of fluorescence produced by a fluorescent material within those channels varies with temperature, the pattern will again be reproduced in the amount of fluorescence emanating from the channel. Thus in the embodiment of FIG. 8, the sinusoidal variation of the temperature of the external surface of the microfluidic device produces a sinusoidal fluorescence variation 810 emanating from the channel. In the embodiment shown in FIG. 8, the fluorescence of the material in the channel decreases as the temperature of the material increases. The delay caused by thermal inertia creates an offset 830 between the time the temperature is at a maximum on the surface and the time the temperature is at a maximum in the channel (as indicated by a minimum fluorescence value). Thus sinusoidally varying the temperature of the surface and monitoring the sinusoidal fluorescence response in the channel allows the time delay caused by thermal intertia to be quantified. The method illustrated in FIG. 8 would work with any fluorescent compound whose fluorescence changes with temperature, regardless of whether the fluorescence increases or decreases with temperature. Furthermore, any other pattern of temperature variations with recognizable features could be used to measure the time delay. For example, instead of a sine wave, the pattern could be a step function or a pulse. Another way to quantify the delay would be to measure the temperature of the surface of the microfluidic device at the moment a melting point probe, which melts at a predetermined temperature, melts. One method of quantifying the temperature offset measured on the surface of the device and the fluid temperature within a channel of the device would be to employ the previously described methods for determining a reference temperature by generating a melting curve for a molecule with a known $T_m$, and determining the temperature at the surface of the microfluidic device when the temperature in the channel is $T_m$.

In joule heating methods, electric current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance: where POWER=power dissipated in fluid: I=electric current passing through fluid; and R=electric resistance of fluid.

$$POWER = I^2 R.$$

The above equation provides a relationship between power dissipated ("POWER") to current ("I") and resistance ("R"). In some of the embodiments of the invention, which are directed toward moving the fluid, a portion of the power goes into kinetic energy of moving the fluid through the channel. Joule heating uses a selected portion of the power to heat the fluid in the channel or a selected channel region(s) of the microfluidic device and can utilize in-channel electrodes. See, e.g., U.S. Pat. No. 5,965,410. This channel region is often narrower or smaller in cross section than other channel regions in the channel structure. The small cross section provides higher resistance in the fluid, which increases the temperature of the fluid as electric current passes therethrough. Alternatively, the electric current can be increased along the length of the channel by increased voltage, which also increases the amount of power dissipated into the fluid to correspondingly increase fluid temperature.

Joule heating permits the precise regional control of temperature and/or heating within separate microfluidic elements of the device of the invention, e.g., within one or several separate channels, without heating other regions where such heating is, e.g., undesirable. Because the microfluidic elements are extremely small in comparison to the mass of the entire microfluidic device in which they are fabricated, such heat remains substantially localized, e.g., it dissipates into and from the device before it affects other fluidic elements. In other words, the relatively massive device functions as a heat sink for the separate fluidic elements contained therein.

To selectively control the temperature of fluid or material of a region of a microchannel, the joule heating power supply of the invention can apply voltage and/or current in several optional ways. For instance, the power supply optionally applies direct current (i.e., DC), which passes through the one region of a microchannel and into another region of the same microchannel that is smaller in cross section in order to heat fluid and material in the second region. This direct current can be selectively adjusted in magnitude to complement any voltage or electric field applied between the regions to move materials in and out of the respective regions. In order to heat the material within a region, without adversely affecting the movement of a material, alternating current (i.e., AC) can be selectively applied by the power supply. The alternating current used to heat the fluid can be selectively adjusted to complement any voltage or electric field applied between regions in order to move fluid in and out of various regions of the device. AC current, voltage, and/or frequency can be adjusted, for example, to heat a fluid without substantially moving the fluid. Alternatively, the power supply can apply a pulse or impulse of current and/or voltage, which will pass through one microchannel and into another microchannel region to heat the fluid in the region at a given instance in time. This pulse can be selectively adjusted to complement any voltage or electric field applied between the regions in order to move materials, e.g., fluids or other materials, in and out of the various regions. Pulse width, shape, and/or intensity can be adjusted, for example, to heat the fluid substantially without moving the fluids or materials, or to heat the material while moving the fluid or materials. Still further, the power supply optionally applies any combination of DC, AC, and pulse, depending upon the application. The microchannel(s) itself optionally has a desired cross section (e.g., diameter, width or depth) that enhances the heating effects of the current passed through it and the thermal transfer of energy from the current to the fluid.

Because electrical energy is optionally used to control temperature directly within the fluids contained in the microfluidic devices, the invention is optionally utilized in microfluidic systems that employ electrokinetic material transport systems, as noted herein. Specifically, the same electrical controllers, power supplies and electrodes can be readily used to control temperature contemporaneously with their control of material transport.

In some embodiments of the invention, the device provides multiple temperature zones by use of zone heating. On such example apparatus is described in Kopp, M. et al. (1998) "Chemical amplification: continuous-flow PCR on a chip" Science 280(5366): 1046-1048. The apparatus described therein consists of a chip with three temperature zones, corresponding to denaturing, annealing, and primer extension temperatures for PCR. The temperature zones can be created by placing the three temperature zones in thermal contact with three different thermal blocks, where each of the three thermal blocks is maintained at a different temperature. A channel fabricated into the chip passes through each zone multiple times to effect a 20 cycle PCR. By changing the flow rate of fluids through the chip, Kopp et al., were able to change the cycle time of the PCR. While devices used for the present invention can be similar to that described by Kopp, they typically differ in significant ways. For example, the reactions performed by Kopp were limited to 20 cycles, which was a fixed aspect of the chip used in their experiments. According to the present invention, reactions optionally comprise any number of cycles (e.g., depending on the parameters of the specific molecules being assayed). Also, the current invention utilizes the thermocycling for, e.g., denaturation and/or renaturation of target/test molecules instead of PCR. For further examples of temperature control in microfluidic devices, see, e.g., U.S. Pat. No. 6,303,343, entitled "Inefficient Fast PCR" by Kopf-Sill, A.; and U.S. Pat. No. 6,403,338, entitled "Microfluidic systems and methods of genotyping" by Knapp, M., et al.

The previously described temperature control methods can be employed to carry out a melting curve analysis in either a stopped flow format or in a continuous flow format. In a stopped flow format, flow is stopped within a microchannel while the temperature in that channel is ramped through the range of temperatures required to generate the desired melt curve. Controlled ramping of the temperature in the channel can be accomplished using any of the joule or non-joule heating methods, possibly in conjunction with an energy sink. The flow stoppage required to generate a melt curve in a stopped flow format typically results in the flow being stopped everywhere else in the microfluidic device. So, it is difficult to integrate a stopped flow format melt analysis with a continuous flow process either upstream or downstream of the melting curve analysis. So, for example, it would be difficult to integrate a stopped flow format melting curve analysis with the continuous flow PCR processes described in U.S. Published Application Nos. 2002/0197630 and 2005/0042639. Thus it would be advantageous to be able to perform a melting curve analysis in a continuous flow format, especially when processes upstream or downstream of the melting curve analysis are continuous flow processes.

In embodiments employing stopped flow format, the controlled ramping of the temperature comprises elevating the temperature of the molecule(s) by continuously increasing the temperature of the molecule(s). For example, the temperature of the molecule(s) can be continuously increased at a rate in the range of 0.1° C./second to 1° C./second. Alternatively, the temperature of the molecule(s) can be continuously increased at a slower rate, such as a rate in the range of 0.01° C./second to 0.1° C./second, or at a faster rate, such as a rate in the range of 1° C./second to 10° C./second.

A melting curve analysis can be performed in continuous flow format through the application of a temperature gradient along the length (i.e. parallel to the direction of flow) of a microchannel. If the melting curve analysis requires that the molecule being analyzed be subjected to a range of temperatures extending from a first temperature to a second temperature, the temperature at one end of the length of the microchannel is controlled to the first temperature, and the temperature at the other end of the length is controlled to the second temperature, thus creating a continuous temperature gradient spanning the temperature range between the first and second selected temperatures. Once a steady state flow of fluid through the portion of the microchannel is established, a corresponding temperature gradient will be established within that fluid. When Joule heating is used, a temperature gradient can be established along the length of a microchannel by fabricating the channel so that it continuously and monotonically changes in cross-sectional area along its length, and then applying a single electric current through that length. Almost any one of the previously described non-joule heating methods, possibly in conjunction with an energy sink, could be used to establish the temperature gradient across the length of the channel. For example, a thermal block can be placed in contact with the length of microchannel over which the temperature gradient is to be established, and two separate peltier elements can be placed at the two ends of the block so as to establish a temperature gradient across the block in the direction corresponding to the length direction of the microchannel.

Figure 9A:
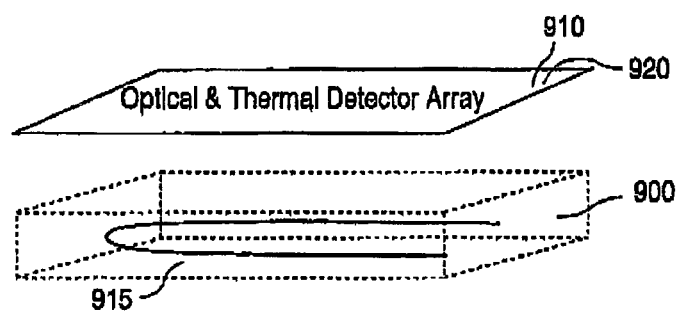
FIGS. 9A-9C schematically depicts a portion of a microfluidic system that may be employed in some embodiments of the invention.
Figure 9B:
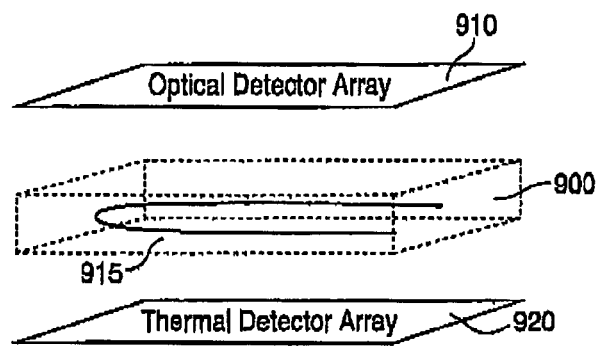
Figure 9C:
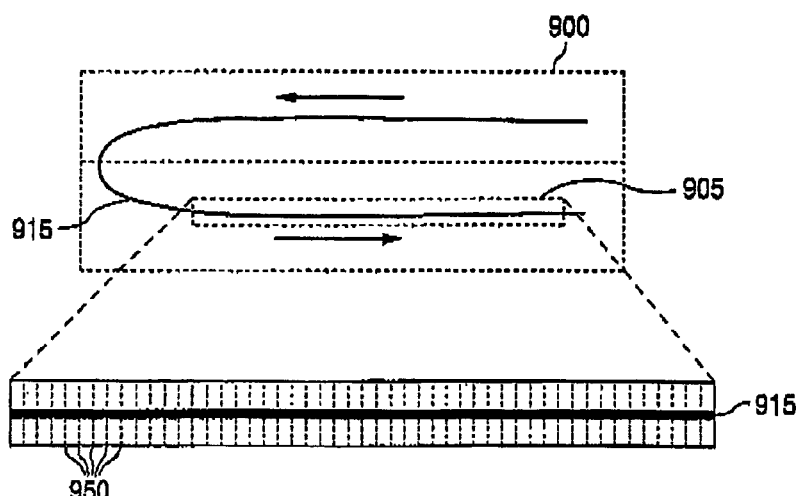

When a temperature gradient spanning the desired range of temperatures is established across the length of the microchannel, all that needs to be done to generate a melting curve is to measure the physical property indicative of binding or denaturation, e.g. fluorescence, at a plurality of points along the channel. In the case of fluorescence, this can be accomplished by placing an array of optical detectors in optical communication with the channel so that the optical array samples the fluorescence at a plurality of points along the length of the channel. In order to generate an accurate melting curve, in particular a curve that is accurate along the temperature axis so that an accurate determination of T, can be made, an array of thermal detectors should also be employed to measure the temperature variation along the length of the microchannel. Schematic representation of two microfluidic systems capable of performing a continuous flow format melting curve analysis are shown in FIGS. 9A, 9B, and 9C. In the system shown in FIG. 9A, the optical detector array 910 and thermal detector array 920 are both disposed above the microfluidic device 900. In the system shown in FIG. 9B, the optical detector array 910 is disposed above the microfluidic device 900, while the thermal detector array 920 is disposed below the microfluidic device. FIG. 9C schematically illustrates how the optical and thermal arrays sample the length 905 of the microfluidic channel 915 to which the thermal gradient is being applied. Within that length 905 of microchannel 915 a temperature and fluorescence measurement is taken where each of the hash marks 950 (only a subset are pointed to) crosses channel 915. Since the temperature varies monotonically from the lowest temperature in the melting curve to the highest temperature of the melting curve along the length 905 of the microchannel, and since each fluorescent reading is taken at the same location as each temperature reading, the combined fluorescence/temperature data taken at each of the plurality of points along the channel will be a data point in the melting curve.

In the embodiments shown in FIGS. 9A-9C, the temperature of the molecule(s) being analyzed are continuously increased, or controllably ramped, as a consequence of the fluid comprising the molecule(s) flowing along the length of the microfluidic channel 915 to which the thermal gradient is being applied. In embodiments where the temperature of the molecule(s) are continuously increased as a result of flow along the length of a channel to which a temperature gradient is applied, the rate at which the temperature of the molecule(s) is continuously increased can be controlled by varying one or more of the temperature gradient, the geometry of the channel (e.g. the cross-sectional area of the channel), or the flow rate of the fluid comprising the molecule(s). By varying the flow rate of the fluid through the channel, the temperature of the molecule(s) can be continuously increased at a variety of rates, including rates in the range of 0.1° C./second to 1° C./second, rates in the range of 0.01° C./second to 0.1° C./second, or rates in the range of 1° C./second to 10° C./second.

The types of optical detectors that can be employed in the optical detector array are discussed below in the "Detectors" section. A variety of different types of temperature detectors can be employed in the thermal detector array. For example, each of the detectors in the array could be a contact temperature detector such as a thermocouple, resistance temperature detector, or thermistor; or a non-contact temperature detector such as an IR thermometer or optical pyrometer. Unless the detector directly samples the fluid in the microchannel, it may be necessary to employ the previously discussed methods for compensating for the difference between measured temperatures and the temperatures in the channels.

As can be seen from the above, the current invention can be configured in many different arrangements depending upon the specific needs of the molecules under consideration. For example, the temperature cycle pattern can be arrayed in numerous ways. Several non-limiting examples include: having the array configured so that different mixtures of molecules flow through a region where temperature is cycled through zones (e.g., going from temperatures where target molecules are predominantly native up to temperatures where the target molecules are predominantly denatured) while continuously monitoring the signal (e.g., the fluorescence, dielectric properties, etc.); configuring the heamow array by measuring the $T_m$ for a molecule and holding the temperature there while monitoring for any ligand-induced change in the signal (e.g., a change in fluorescence, dielectric properties, etc.); and cycling the temperature from the $T_m$ and monitoring for any ligand-induced change in the signal (e.g., a change in fluorescence, etc.) (such method is helpful in avoiding bubble problems). Again, the above non-limiting illustrations are only examples of the many different configurations/embodiments of the invention.

Fluid Flow

A variety of controlling instrumentation is optionally utilized in conjunction with the microfluidic devices described above, for controlling the transport and direction of fluidic materials and/or materials within the devices of the present invention, e.g., by pressure-based or electrokinetic control.

In the present system, the fluid direction system controls the transport, flow and/or movement of samples (e.g., test molecules and target molecules), reagents (e.g., substrates), etc. through the microfluidic device. For example, the fluid direction system optionally directs the movement of one or more samples of molecules into a first microchannel, where the molecules are optionally incubated. It also optionally directs the simultaneous or sequential movement of one or more samples into a detection region and optionally to and from, e.g., reagent reservoirs.

The fluid direction system also optionally directs the loading and unloading of the plurality of samples in the devices of the invention. The fluid direction system also optionally iteratively repeats these movements to create high throughput screening, e-g., of thousands of samples. Alternatively, the fluid direction system repeats the movements to a lesser degree of iterations, or low throughput screening (applied, e.g., when the specific analysis under observation requires, e.g., a long incubation time when a high throughput format would be counter productive) or the fluid direction system utilizes a format of high throughput and low throughput screening depending on the specific requirements of the assay. Additionally, the devices of the invention optionally use a multiplex format to achieve high throughput screening, e.g., through use of a series of multiplexed pipettor devices or multiplexed system of channels coupled to a single controller for screening in order to increase the amount of samples analyzed in a given period of time.

One method of achieving transport or movement of particles through microfluidic channels is by electrokinetic material transport. In general, electrokinetic material transport and direction systems include those systems that rely upon the electrophoretic mobility of charged species within the electric field applied to the structure. Such systems are more particularly referred to as electrophoretic material transport systems.

Electrokinetic material transport systems, as used herein, include systems that transport and direct materials within a microchannel containing structure, through the application of electrical fields to the materials, thereby causing material movement through and among the microchannel and/or microchambers, e.g., cations will move toward a negative electrode, while anions will move toward a positive electrode. Movement of fluids toward or away from a cathode or anode can cause movement of particles suspended within the fluid (or even particles over which the fluid flows). Similarly, the particles can be charged, in which case they will move toward an oppositely charged electrode (indeed, it is possible to achieve fluid flow in one direction while achieving particle flow in the opposite direction). In some embodiments of the present invention, the fluid can be immobile or flowing.

For optional electrophoretic applications of the present invention, the walls of interior channels of the electrokinetic transport system are optionally charged or uncharged. Typical electrokinetic transport systems are made of glass, charged polymers, and uncharged polymers. The interior channels are optionally coated with a material which alters the surface charge of the channel. A variety of electrokinetic controllers are described, e.g., in Ramsey WO 96/04547, Parce et al. WO 98/46438 and Dubrow et al., WO 98/49548, as well as in a variety of other references noted herein.

To provide appropriate electric fields, the system of the microfluidic device optionally includes a voltage controller that is capable of applying selectable voltage levels, simultaneously, to each of the various microchannels and microchambers, and including the ground. Such a voltage controller is optionally implemented using multiple voltage dividers and multiple relays to obtain the selectable voltage levels. Alternatively, multiple independent voltage sources are used. The voltage controller is electrically connected to each of the device's fluid conduits via an electrode positioned or fabricated within each of the plurality of fluid conduits (e.g., microchannels, etc.). In one embodiment, multiple electrodes are positioned to provide for switching of the electric field direction in the microchannel(s), thereby causing the analytes to travel a longer distance than the physical length of the microchannel. Use of electrokinetic transport to control material movement in interconnected channel structures was described in, e.g., WO 96/94547 to Ramsey. An exemplary controller is described in U.S. Pat. No. 5,800,690. Modulating voltages are concomitantly applied to the various fluid areas of the device to affect a desired fluid flow characteristic, e.g., continuous or discontinuous (e.g., a regularly pulsed field causing the sample to oscillate direction of travel) flow of labeled components toward a waste reservoir. Particularly, modulation of the voltages applied at the various areas can move and direct fluid flow through the interconnected channel structure of the device.

The controlling instrumentation discussed above is also optionally used to provide for electrokinetic injection or withdrawal of material downstreak of the region of interest to control an upstream flow rate. The same instrumentation and techniques described above are also utilized to inject a fluid into a downstream port to function as a flow control element.

The current invention also optionally includes other methods of transport, e.g., available for situations in which electrokinetic methods are not desirable. For example, fluid transport and direction, sample introduction and reaction, etc. are optionally carried out in whole, or in part, in a pressure-based system to avoid electrokinetic biasing during sample mixing. High throughput systems typically use pressure induced sample introduction. Pressure based flow is also desirable in systems in which electrokinetic transport is also used. For example, pressure based flow is optionally used for introducing and reacting reagents in a system in which the products are electrophoretically separated. In the present invention molecules are optionally loaded and other reagents are flowed through the microchannels using, e.g., electrokinetic fluid control and/or under pressure.

Pressure is optionally applied to the microscale elements of the invention, e.g., to a microchannel, microchamber, region, or reservoir, to achieve fluid movement using any of a variety of techniques. Fluid flow and flow of materials suspended or solubilized within the fluid, including cells or molecules, is optionally regulated by pressure based mechanisms such as those based upon fluid displacement, e.g., using a piston, pressure diaphragm, vacuum pump, probe or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, e.g., a plunger fitted into a material reservoir, for forcing material through a channel or other conduit', or is a combination of such forces. Internal sources include microfabricated pumps, e.g., diaphragm pumps, thermal pumps, lamb wave pumps and the like that have been described in the art. See, e.g., U.S. Pat. Nos. 5,271,724; 5,277,566; and 5,375,979 and Published PCT Application Nos. WO 94/05414 and WO 97/02347.

In some embodiments, a pressure source is applied to a reservoir or well at one end of a microchannel to force a fluidic material through the channel. Optionally, the pressure can be applied to multiple ports at channel termini, or, a single pressure source can be used at a main channel terminus. Optionally, the pressure source is a vacuum source applied at the downstream terminus of the main channel or at the termini of multiple channels. Pressure or vacuum sources are optionally supplied externally to the device or system, e.g., external vacuum or pressure pumps sealably fitted to the inlet or outlet of channels, or they are internal to the device, e.g., microfabricated pumps integrated into the device and operably linked to channels or they are both external and internal to the device. Examples of microfabricated pumps have been widely described in the art. See, e.g., published International Application No. WO 97/02357.

These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or, by applying a single vacuum at a common waste port and configuring the various channels with appropriate resistance to yield desired flow rates. Example systems are described in U.S. Ser. No. 09/238,467 filed Jan. 28, 1999. In the present invention, for example, vacuum sources optionally apply different pressure levels to various channels to switch flow between the channels. As discussed above, this is optionally done with multiple sources or by connecting a single source to a valve manifold comprising multiple electronically controlled valves, e.g., solenoid valves.

In embodiments in which a stopped-flow format method is employed to generate a melting curve, it is important that the flow within the microchannel in which the melting curve is being generated be completely stopped to maintain the integrity of the sample being analyzed. Changes in the fluorescent characteristics of the sample caused by photobleaching can be employed to determine whether the flow through the microchannel is completely stopped. The amount of photobleaching in a flowing liquid is lower than the amount of photobleaching in a stagnant fluid simply because the fluorescent moieties in the flowing liquid are exposed to the excitation light for a shorter amount of time because the moeities are moving through the detection zone. Accordingly, the level of photobleaching is indicative of whether the fluid comprising the fluorescent moieties is moving or static within the microchannel. For example, if the exact driving force required to completely stop flow, i.e. to produce a zero flow rate, within a microfluidic channel is unknown, a range of driving forces encompassing the exact driving force could be applied to the channel. If the fluid within the microfluidic channel contains a fluorescent material, and if the light used to excite the fluorescent material is intense enough to photobleach the fluorescent material, then the maximum degree of photobleaching of the fluorescent material will occur when the flow rate of the fluid through the channel is zero. Maximizing the amount of photobleaching minimizes the amount of fluorescence produced by the fluorescent material. Therefore the driving force that corresponds to a zero flow rate is the driving force that produces the minimum amount of fluorescence.

Hydrostatic, wicking and capillary forces are also optionally used to provide fluid pressure for continuous fluid flow of materials such as enzymes, substrates, modulators, or protein mixtures in the invention. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In using wicking/capillary methods, an adsorbent material or branched capillary structure is placed in fluidic contact with a region where pressure is applied, thereby causing fluid to move towards the adsorbent material or branched capillary structure. The capillary forces are optionally used in conjunction with electrokinetic or pressure-based flow in the present invention. The capillary action pulls material through a channel. For example a wick is optionally added to draw fluid through a porous matrix fixed in a microscale channel or capillary.

The present invention optionally includes mechanisms for reducing adsorption of materials during fluid-based flow, e.g., as are described in "PREVENTION OF SURFACE ADSORPTION IN MICROCHANNELS BY APPLICATION OF ELECTRIC CURRENT DURING PRESSURE-INDUCED FLOW" filed May 11, 1999 by Parce et al. In brief, adsorption of components, proteins, enzymes, markers and other materials to channel walls or other microscale components during pressure-based flow can be reduced by applying an electric field such as an alternating current to the material during flow. Alternatively, flow rate changes due to adsorption are detected and the flow rate is adjusted by a change in pressure or voltage.

The invention also optionally includes mechanisms for focusing labeling reagents, enzymes, modulators, and other components into the center of microscale flow paths, which is useful in increasing assay throughput by regularizing flow velocity, e.g., in pressure based flow, e.g., as are described in "FOCUSING OF MICROPARTICLES IN MICROFLUIDIC SYSTEMS" by H. Garrett Wada et al., filed May 17, 1999. In brief, sample materials are focused into the center of a channel by forcing fluid flow from opposing side channels into the main channel, or by other fluid manipulation.

In an alternate embodiment, microfluidic systems of the invention can be incorporated into centrifuge rotor devices, which are spun in a centrifuge. Fluids and particles travel through the device due to gravitational and centripetal/centrifugal pressure forces.

Fluid flow or particle flow in the present devices and methods is optionally achieved using any one of the above techniques, alone or in combination. Typically, the controller systems involved are appropriately configured to receive or interface with a microfluidic device or system element as described herein. For example, the controller, optionally includes a stage upon which the device of the invention is mounted to facilitate appropriate interfacing between the controller and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

Detection

In general, detection systems in microfluidic devices include, e.g., optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more microchannels, microchambers or conduits of the device, such that the detector is within sensory communication with the device, channel, or chamber. The phrase "proximal," to a particular element or region, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Many different molecular/reaction characteristics can be detected in microfluidic devices of the current invention. For example, one embodiment detects fluorescence or emitted light. Another embodiment detects changes in the thermal parameters (e.g., heat capacity, etc.) involved in the assays.

Examples of detection systems in the current invention can include, e.g., optical detection systems for detecting an optical property of a material within the microchannels and/or microchambers of the microfluidic devices that are incorporated into the microfluidic systems described herein. Such optical detection systems are typically placed adjacent to a microscale channel of a microfluidic device, and optionally are in sensory communication with the channel via an optical detection window or zone that is disposed across the channel or chamber of the device.

Optical detection systems of the invention include, e.g., systems that are capable of measuring the light emitted from material within the channel, the transmissivity or absorbance of the material, as well as the material's spectral characteristics, e.g., fluorescence, chemiluminescence. Detectors optionally detect a labeled compound, such as fluorographic, colorimetric and radioactive components. Types of detectors optionally include spectrophotometers, photodiodes, avalanche photodiodes, microscopes, scintillation counters, cameras, diode arrays, imaging systems, photomultiplier tubes, CCD arrays, scanning detectors, galvo-scanners, film and the like, as well as combinations thereof. Proteins, antibodies, or other components that emit a detectable signal can be flowed past the detector, or alternatively, the detector can move relative to an array to determine molecule position (or, the detector can simultaneously monitor a number of spatial positions corresponding to channel regions, e.g., as in a CCD array). Examples of suitable detectors are widely available from a variety of commercial sources known to persons of skill. See, also, The Photonics Design and Application Handbook, books 1, 2, 3 and 4, published annually by Laurin Publishing Co., Berkshire Common, P.O. Box 1146, Pittsfield, Mass. for common sources for optical components.

As noted above, the present devices include, as microfluidic devices typically do, a detection window or zone at which a signal, e.g., fluorescence, is monitored. This detection window or zone optionally includes a transparent cover allowing visual or optical observation and detection of the assay results, e.g., observation of a colorimetric, fluorometric or radioactive response, or a change in the velocity of colorimetric, fluorometric or radioactive component.

Another optional embodiment of the present invention involves use of fluorescence correlation spectroscopy and/or confocal nanofluorimetric techniques to detect fluorescence from the molecules in the microfluidic device. Such techniques are easily available (e.g., from Evotec, Hamburg, Germany) and involve detection of fluorescence from molecules that diffuse through the illuminated focus area of a confocal lens. The length of any photon burst observed will correspond to the time spent in the confocal focus by the molecule. The diffusion coefficient of the molecules passing through this area can be used to measure, e.g., degree of binding. Various algorithms used for analysis can be used to evaluate fluorescence signals from individual molecules based on changes in, e.g., brightness, fluorescence lifetime, spectral shift, FRET, quenching characteristics, etc.

As stated above, the sensor or detection portion of the devices and methods of the present invention can optionally comprise a number of different apparatuses. For example, fluorescence can be detected by, e.g., a photomultiplier tube, a charge coupled device (CCD) (or a CCD camera), a photodiode, or the like.

A photomultiplier tube is an optional aspect of the current invention. Photomultiplier tubes (PMTs) are devices which convert light (photons) into electronic signals. The detection of each photon by the PMT is amplified into a larger and more easily measurable pulse of electrons. PMTs are commonly used in many laboratory applications and settings and are well known to those in the art.

Another optional embodiment of the present invention comprises a charge coupled device. CCD cameras are very useful in that they can detect even very small amounts of electromagnetic energy (e.g., such that emitted by fluorophores in the present invention). CCD cameras are made from semi-conducting silicon wafers that release free electrons when light photons strike the wafers. The output of electrons is linearly directly proportional to the amount of photons that strike the wafer. This allows the correlation between the image brightness and the actual brightness of the event observed. CCD cameras are very well suited for imaging of fluorescence emissions since they can detect even extremely faint events, can work over a broad range of spectrum, and can detect both very bright and very weak events. CCD cameras are well know to those in the art and several suitable examples include those made by: Stratagene (La Jolla, Calif.), Alpha-Innotech (San Leandro, Calif.), and Apogee Instruments (Tucson, Ariz.) among others.

Yet another optional embodiment of the present invention comprises use of a photodiode to detect fluorescence from the molecules in the microfluidic device. Photodiodes absorb incident photons that cause electrons in the photodiode to diffuse across a region in the diode thus causing a measurable potential difference across the device. This potential can be measured and is directly related to the intensity of the incident light.

In some aspects, the detector measures an amount of light emitted from the material, such as a fluorescent or chemiluminescent material. As such, the detection system will typically include collection optics for gathering a light based signal transmitted through the detection window or zone, and transmitting that signal to an appropriate light detector. Microscope objectives of varying power, field diameter, and focal length are readily utilized as at least a portion of this optical train. The detection system is typically coupled to a computer (described in greater detail below), via an analog to digital or digital to analog converter, for transmitting detected light data to the computer for analysis, storage and data manipulation.

In the case of fluorescent materials such as labeled cells or fluorescence indicator dyes or molecules, the detector optionally includes a light source which produces light at an appropriate wavelength for activating the fluorescent material, as well as optics for directing the light source to the material contained in the channel or chamber. The light source can be any number of light sources that provides an appropriate wavelength, including lasers, laser diodes and LEDs. Other light sources are optionally utilized for other detection systems. For example, broad band light sources for light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with a computer (described below), by permitting the use of few or a single communication port(s) for transmitting information between the controller, the detector and the computer. Integration of the detection system with a computer system typically includes software for converting detector signal information into assay result information, e.g., concentration of a substrate, concentration of a product, presence of a compound of interest, or the like.

In another aspect of the current invention, monitoring of the physical changes in molecules in the invention is achieved using a calorimetric detection system. In calorimetric assays, a change in heat capacity is measured as molecules undergo unfolding due to changes in temperature. Titration calorimetry and/or differential scanning calorimetry is optionally used to determine the thermal parameters of a test molecule for a target molecule in the invention. See, e.g., Brandts, J. et al. (1990) "Study of strong to ultratight protein interactions using differential scanning calorimetry" Biochem 29(29):6927-6940. calorimetric measurement devices are available from a number of sources and their calibration and use are well known to those versed in the art.

Computer

As noted above, either or both of the fluid direction system and/or the detection system are coupled to an appropriately programmed processor or computer that functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer optionally includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

For example, the computer is optionally used to direct a fluid direction system to control fluid flow, e.g., through a variety of interconnected channels. The fluid direction system optionally directs the movement of at least a first member of a plurality of molecules into a first member of a plurality of channels concurrent with directing the movement of at least a second member of the plurality of molecules into one or more detection channel regions. The fluid direction system also directs the movement of at least a first member of the plurality of molecules into the plurality of channels concurrent with incubating at least a second member of the plurality of molecules. It also directs movement of at least a first member of the plurality of molecules into the one or more detection channel regions concurrent with incubating at least a second member of the plurality of molecules.

By coordinating channel switching, the system directs the movement of at least one member of the plurality of molecules into the plurality of microchannels and/or one member into a detection region at a desired time interval, e.g., greater than 1 minute, about every 60 seconds or less, about every 30 seconds or less, about every 10 seconds or less, about every 1.0 seconds or less, or about every 0.1 seconds or less. Each sample, with appropriate channel switching as described above, remains in the plurality of channels for a desired period of time, e.g., between about 0.1 minutes or less and about 60 minutes or more. For example the samples optionally remain in the channels for a selected incubation time of, e.g., 20 minutes.

The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring and control of materials in the channels. For example, the software directs channel switching to control and direct flow as described above. Additionally the software is optionally used to control electrokinetic or pressure-modulated injection or withdrawal of material. The injection or withdrawal is used to modulate the flow rate as described above. The computer also typically provides instructions, e.g., to the controller or fluid direction system for switching flow between channels to achieve a high throughput format.

In addition, the computer optionally includes software for deconvolution of the signal or signals from the detection system. For example, the deconvolution distinguishes between two detectably different spectral characteristics that were both detected, e.g., when a substrate and product comprise detectably different labels.

Any controller or computer optionally includes a monitor which is often a cathode ray tube ("CRT") display, a flat panel display (e.g., active matrix liquid crystal display, liquid crystal display), or the like. Data produced from the microfluidic device, e.g., thermal property curves from binding assays, is optionally displayed in electronic form on the monitor. Additionally, the data, e.g., thermal property curves, or other data, gathered from the microfluidic device can be outputted in printed form. The data, whether in printed form or electronic form (e.g., as displayed on a monitor), can be in various or multiple formats, e.g., curves, histograms, numeric series, tables, graphs and the like.

Computer circuitry is often placed in a box which includes, e.g., numerous integrated circuit chips, such as a microprocessor, memory, interface circuits. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

Example Integrated Systems

Figure 1B:
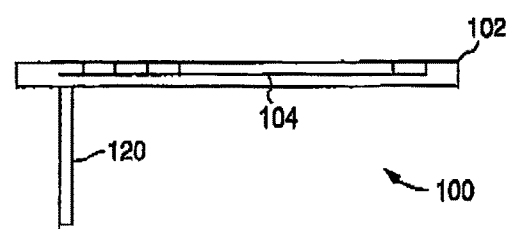
Figure 1C:
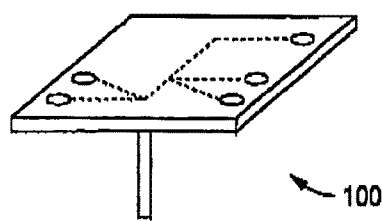
Figure 2:
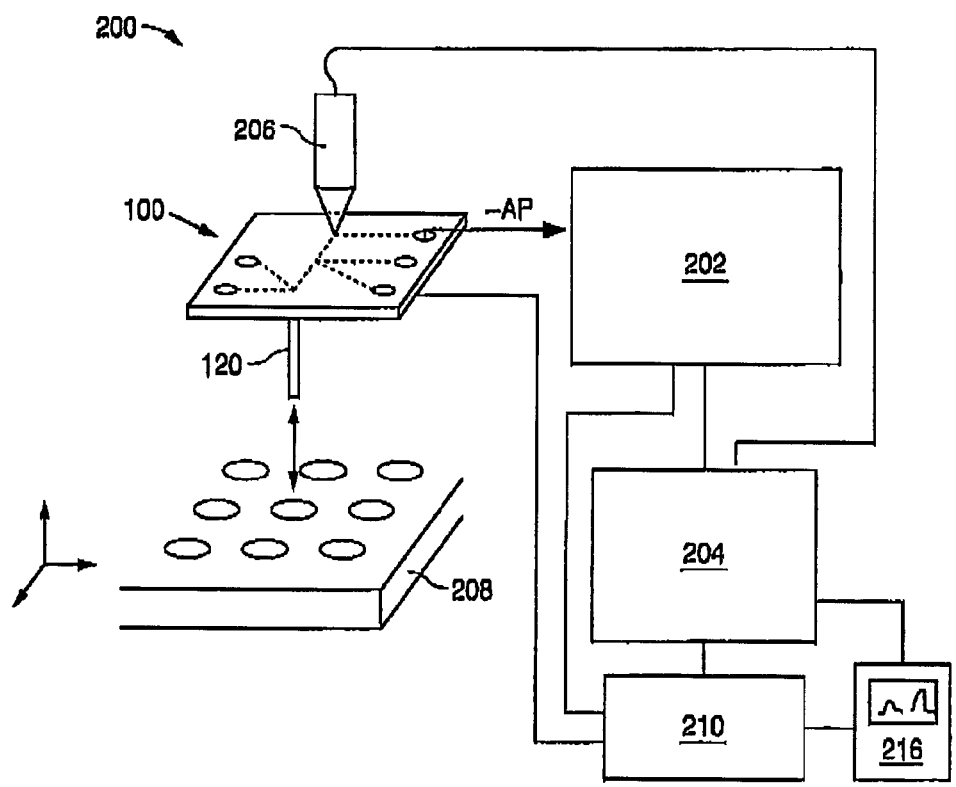
FIG. 2 is a schematic of a system comprising a computer, detector and temperature controller.

FIG. 1, Panels A, B, and C and FIG. 2 provide additional details regarding example integrated systems that are optionally used to practice the methods herein. An integrated system in accordance with the invention comprises a microfluidic device 100 that is a replaceable component, like a cartridge or cassette, that is interfaced with an instrument 200. The microfluidic device shown in FIGS. 1 and 2 comprises a body structure 102 that has a main channel 104 disposed therein. A sample or mixture of components is optionally flowed from pipettor 120 towards reservoir 114, e.g., by applying a vacuum at reservoir 114 (or another point in the system) or by applying appropriate voltage gradients. Accordingly, the pipettor represents the farthest upstream point in the fluid flow path, while reservoir 114 represent the farthest downstream point in the fluid flow path. Alternatively, a vacuum is applied at, e.g., reservoirs 108, 112 or through pipettor channel 120. Additional materials, such as buffer solutions, substrate solutions, enzyme solutions, test molecules, fluorescence indicator dyes or molecules, and the like as described herein are optionally flowed from wells, e.g., 108 or 112 and into main channel 104. Flow from these wells is optionally performed by modulating fluid pressure, or by electrokinetic approaches as described (or both). As fluid is added to main channel 104, e.g., from reservoir 108, the flow rate increases. The flow rate is optionally reduced by flowing a portion of the fluid from main channel 104 into flow reduction channel 106 or 110. The arrangement of channels depicted in FIG. 1 is only one possible arrangement out of many which are appropriate and available for use in the present invention. Additional alternatives can be devised, e.g., by combining the microfluidic elements described herein, e.g., flow reduction channels, with other microfluidic devices described in the patents and applications referenced herein.

Samples and materials are optionally flowed from the enumerated wells or from a source external to the body structure. As depicted, the integrated system optionally includes pipettor channel 120, e.g., protruding from body 102, for accessing a source of materials external to the microfluidic system. Typically, the external source is a microtiter dish or other convenient storage medium. For example, as depicted in FIG. 2, pipettor channel 120 can access microwell plate 208, which includes sample materials (e.g., test molecules and/or target molecules), buffers, substrate solutions, fluorescence indicator dyes or molecules, enzyme solutions, and the like, in the wells of the plate.

The instrument 200 that interfaces with the microfluidic device 100 can perform a variety of different functions: supplying the driving forces that propel fluid through the channels in the chip, monitoring and controlling conditions (e.g., temperature) within the channels of the microfluidic device, detecting signals emanating from the chip, introducing fluids into and extracting fluids out of the chip, and possibly many others. Instruments 200 in accordance with the invention are typically computer controlled so that they can be programmed to interface with different types of microfluidic devices, and/or to carry out desired processes within a particular microfluidic device. The microfluidic device typically interfaces with an instrument in the manner described in U.S. Pat. Nos. 5,955,028; 6,071,478; 6,399,023; and 6,399,025.

Detector 206 is in sensory communication with channel 104, detecting signals resulting, e.g., from labeled materials flowing through the detection region, changes in heat capacity or other thermal parameters, etc. Detector 206 is optionally coupled to any of the channels or regions of the device where detection is desired. Detector 206 is operably linked to computer 204, which digitizes, stores, and manipulates signal information detected by detector 206, e.g., using any of the instructions described above, e.g., or any other instruction set, e.g., for determining concentration, molecular weight or identity, or the like.

Fluid direction system 202 controls voltage, pressure, or both, e.g., at the wells of the systems or through the channels of the system, or at vacuum couplings fluidly coupled to channel 104 or other channel described above. Optionally, as depicted, computer 204 controls fluid direction system 202. In one set of embodiments, computer 204 uses signal information to select further parameters for the microfluidic system. For example, upon detecting the presence of a component of interest in a sample from microwell plate 208, the computer optionally directs addition of a potential modulator of component of interest into the system.

Temperature control system 210 controls joule and/or non-joule heating at the wells of the systems or through the channels of the system as described herein. Optionally, as depicted, computer 204 controls temperature control system 210. In one set of embodiments, computer 204 uses signal information to select further parameters for the microfluidic system. For example, upon detecting the desired temperature in a sample in channel 104, the computer optionally directs addition of, e.g., a potential binding molecule (i.e., test molecule) or fluorescence indicator dye or molecule into the, system.

Monitor 216 displays the data produced by the microfluidic device, e.g., thermal property curves generated from binding assays. Optionally, as depicted, computer 204 controls monitor 216. Additionally, computer 204 is connected to and directs additional components such as printers, electronic data storage devices and the like.

Figure 10:
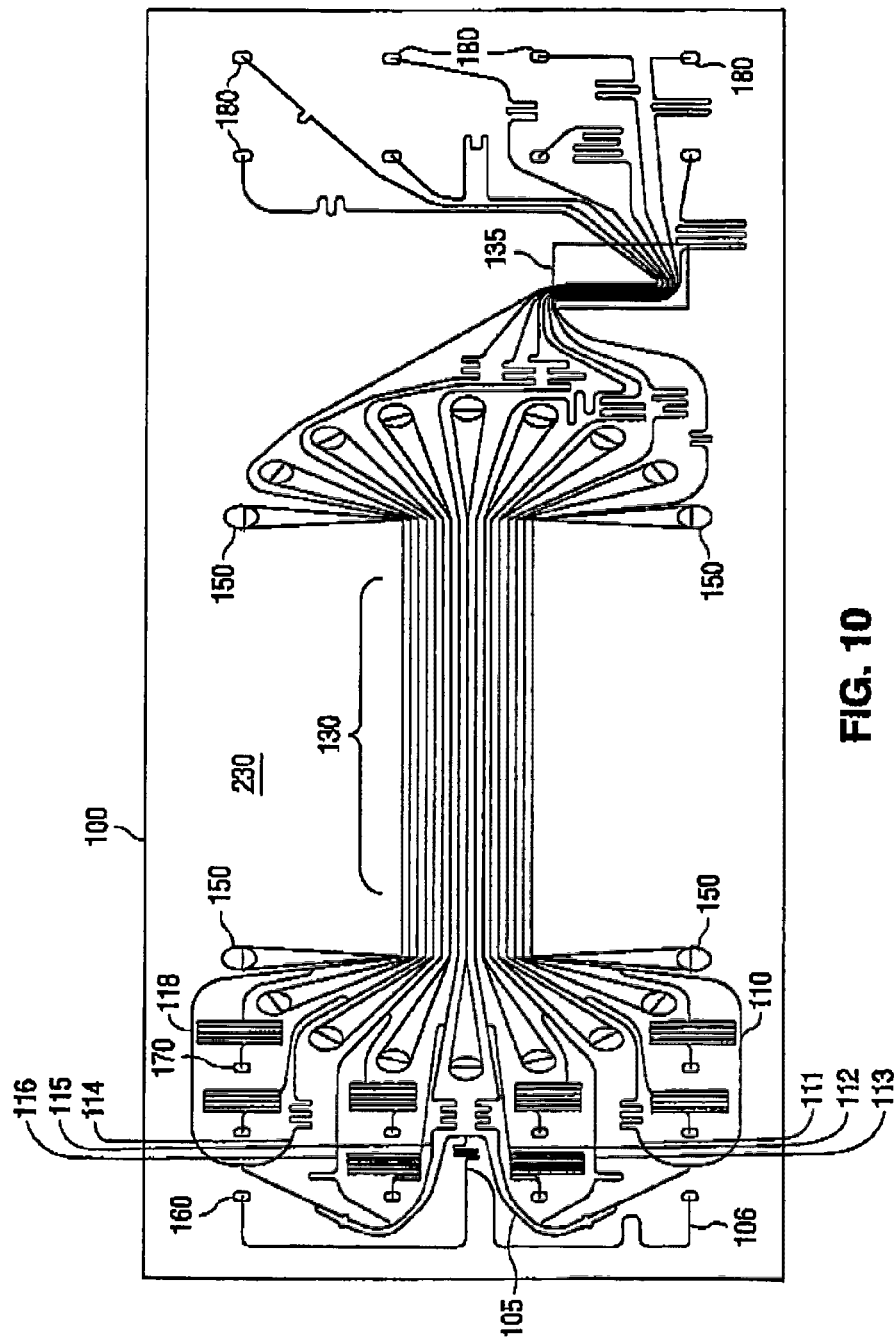
FIG. 10 shows a microfluidic device capable of performing continuous flow PCR followed by melting curve analysis of the amplicons.
Figure 11A:
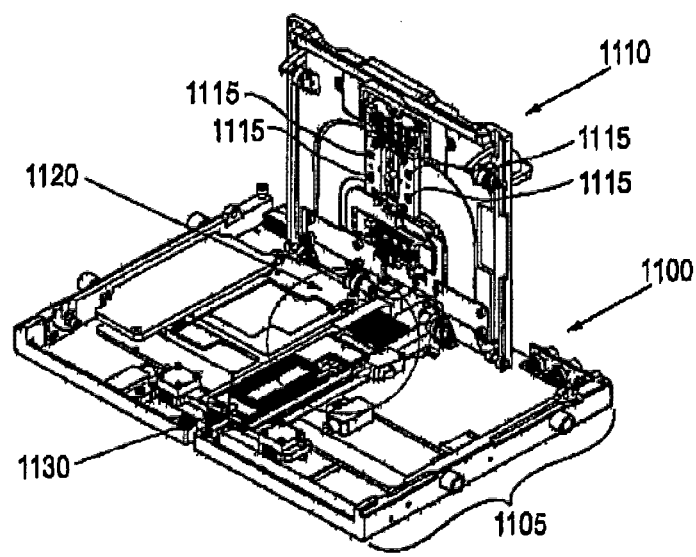
FIGS. 11A-11D show the portion of an integrated system that interfaces with the microfluidic device of FIG. 10.
Figure 11B:
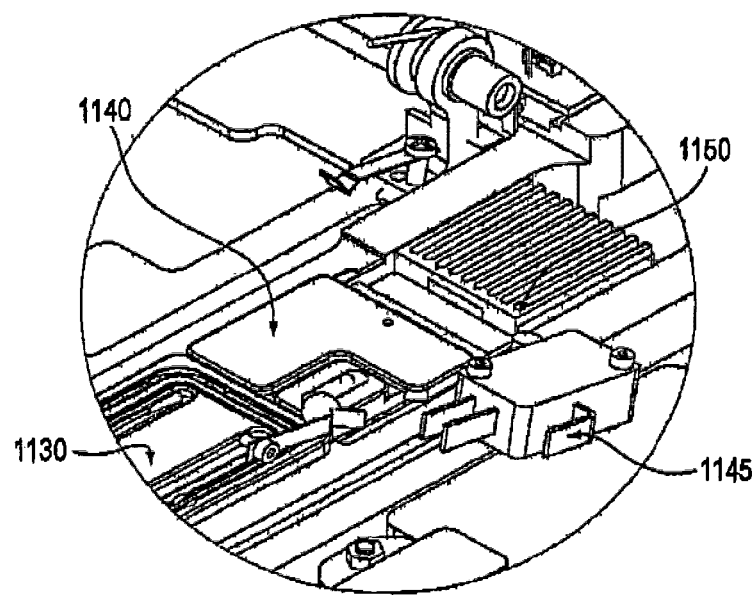
Figure 11C:
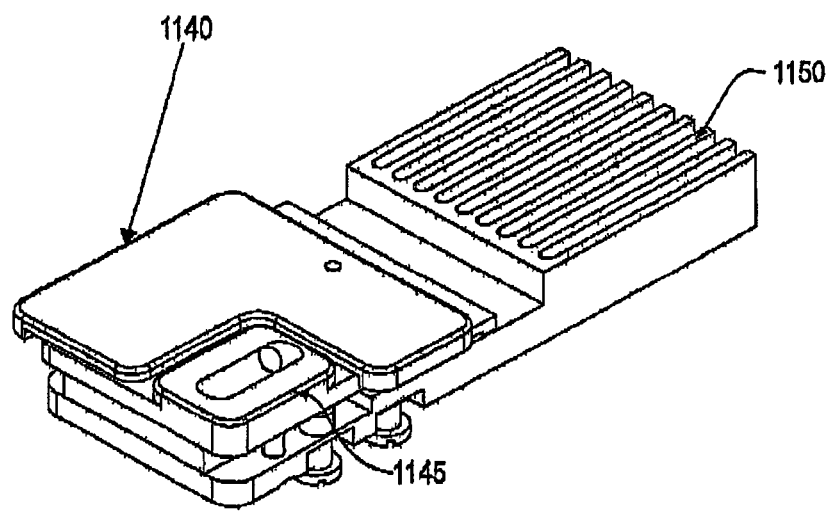
Figure 11D:
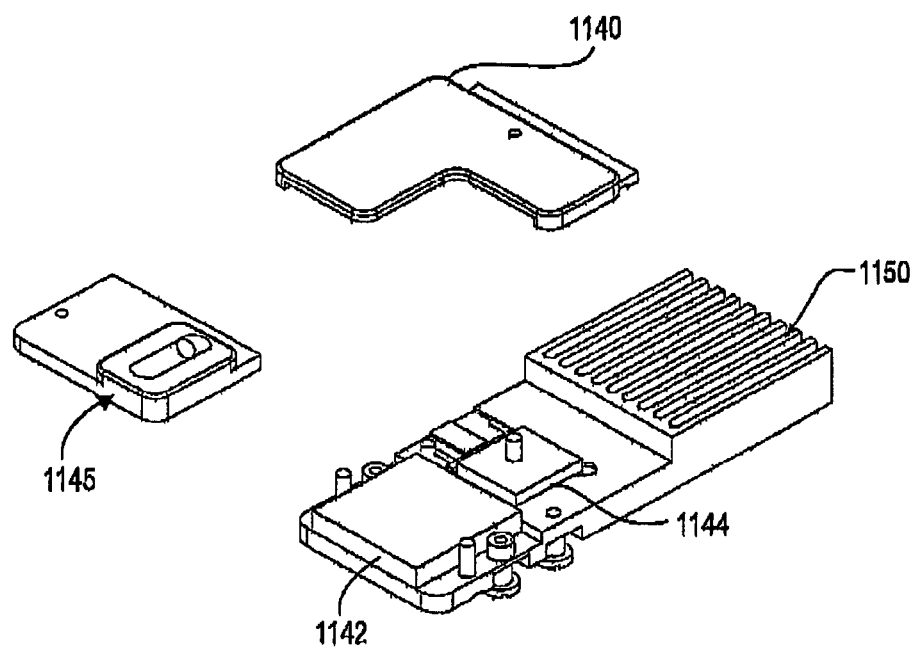

An example of a specific microfluidic device 100 that could be employed in the system in FIG. 2 is shown in FIG. 10. This microfluidic device is capable of performing both continuous flow PCR and melting curve analysis. The operation of the continuous flow PCR portion of the device is described in detail in U.S. Published Application Nos. 2002/0197630 and 2005/0042639. In short, the continuous flow PCR process involves using a microfluidic pipettor chip as shown in the chip design schematic of FIGS. 1 and 2 to bring a DNA sample (e.g., a genomic DNA) onto chip 100 through a pipettor using a pressure gradient into distribution channel 105. Under continuous flow, in an assembly-line fashion, the sample was first mixed with a common reagent from an on-chip reagent reservoir through common reagent channel 106, then split into 8 equal aliquots into 8 independent analysis channels 110-118. Each aliquot was mixed with locus-specific reagents supplied from a channel-specific chip reservoir to form a reaction mixture, then flowed through heated region 130 comprising metal traces proximal to amplification microchannel 110-118 to provide controlled heated regions of chip 100. Reagent addition for channel specific reagents into channels 110-118 provides an elegant microfluidic method of providing for an on-chip "hot start," in which all of the reagents are added to analysis channels just before amplification. The temperature of the region is cycled appropriately (temperature set points and respective dwell times are controlled) for PCR conditions in the channels in heated region 130. Heated channel lengths and fluid velocity are chosen such that the total PCR cycles meet a desired number, usually between 25 to 40 cycles (though inefficient PCR approaches that have short cycle times and high cycle numbers can also be used.

After PCR amplification, the amplicons can be characterized by performing melting curve analysis within the length of the eight channels within detection region 135. In some embodiments, the melting curve analysis could be performed by stopping flow within the channels traversing detection region 135, and then ramping the temperature within detection region 135 by using any of the previously described temperature control methods. The extent of denaturation can be monitored using any of the previously described detectable properties. In alternative embodiments, the melting curve analysis could be performed using a continuous flow format melting curve analysis carried out along the length of each of the eight channels traversing detection region 135. As illustrated in the embodiments shown in FIGS. 9A-9C, a melting curve analysis of the amplicons can be performed in a continuous flow process by flowing a fluid containing the amplicons through a microfluidic channel that has a thermal gradient imposed along its length. Accordingly, a continuous flow format melting curve analysis could be performed in the device shown in FIG. 10 by applying a temperature gradient along the length of the eight channels traversing detection region 135.

In one illustrative embodiment, a continuous flow format melting curve analysis is performed in the microfluidic device shown in FIG. 10 by placing the device into an integrated system comprising the interface module 1100 shown in FIGS. 11A-D. The interface module 1100 comprises a base portion 1105 and a clam-shell type lid 1110. The interface module 1100 is configured to receive the microfluidic device of FIG. 10 within a receiving region of the base portion 1105 that is generally within the circled area 1120 in FIG. 11A. Once the microfluidic device is placed on top of the receiving region 1120 of the base portion, the lid 1110 is closed so that at least some of the wells (e.g., 160, 170, 180) at the termini of the various channels (e.g. 110-118) engage interface elements 1115 on the lid. These interface elements provide the driving forces, such as voltage or pressure, that propel fluid through the channels of the microfluidic device. Other interface elements 1115 on the lid 1110 make electrical contact with the termini 150 of the metal traces that are used as resistive heating elements in the heated region 130 of the microfluidic device. The receiving region 1120 of the base-plate 1105 can comprise a plurality of temperature control systems that independently manipulate the temperature of different regions of the microfluidic device. The temperature control systems in the embodiment of FIGS. 11A-11D are shown in increasing levels of detail in FIGS. 11B-11D. One temperature control system comprises a fluid passage 1130 that forms a sealed fluid path when a microfluidic device is placed on the receiving region 1120 and held in place by the closure of lid 1110. The interface module 1100 is configured so that the fluid passage 1130 is directly underneath the heated region 130 of the microfluidic device. The thermal cycling required for PCR is accomplished by passing electrical current through the metal traces to heat the portion of the channels 110-118 that pass through the heated region 130, while the fluid contacting the backside of the microfluidic device is alternatively employed to rapidly cool that portion of the channels. A second temperature control system is used to separately control the temperatures of the portion 135 of the microfluidic device in which a thermal melt analysis is performed, and the portion of the microfluidic device containing waste wells 180. The second temperature control system comprises a first thermal block 1140 that contacts the portion of the backside of the microfluidic device opposite the waste wells 180, and a second thermal block 1145 that contacts the portion of the backside of the microfluidic device underlying the analysis portion 135 of the microfluidic device. As can be best seen in the exploded view of FIG. 11D, the first thermal block 1140 is in thermal contact with a first thermoelectric cooling device 1144 (i.e., a peltier device), while the second thermal block 1145 is in thermal contact with a second thermoelectric cooling device 1142. The two thermoelectric cooling devices 1142, 1144 can be independently controlled, thus providing independent temperature control for the analysis portion 135 and the waste well 180 portions of the microfluidic device.

In an illustrative embodiment, the first thermoelectric cooling device 1144 is used to control the temperature of the waste well 180 region of the microfluidic device to a constant temperature of 25° C. The second thermoelectric cooling device 1142 is used to ramp the temperature of the analysis region 135 of the microfluidic device from 60° C. to 95° C., at a rate within the range of 0.1° C./s to 1.0° C./s inclusive, so that a stopped-flow type thermal melt analysis can be performed on amplicons present within the channels within the analysis region 135.

One feature of the interface module 1100 that facilitates independent temperature control of the waste well and analysis regions of the microfluidic device is that the first 1140 and second 1145 thermal blocks are separated by an air gap, which inhibits heat transfer between the first and second thermal blocks. Although the two thermal blocks 1140, 1145 are separated by an air gap, the two thermoelectric heaters 1142, 1144 are both attached to a common heat sink 1150. The use of a common heat sink 1150 provides benefits over the use of separate heat sinks in embodiments in which the temperature setpoint of the analysis region 135 is higher than the temperature setpoint of the waste well 180 region. These benefits arise because the heat is typically removed from the waste well portion of the microfluidic device in order to maintain that portion at a constant temperature of 25° C., while heat must be added to the analysis portion of the microfluidic device in order to reach the temperature required to perform thermal melt analysis. Since the heat sink 1150 removes heat from one thermoelectric cooler and adds heat to the other thermoelectric cooler, the temperature tends to stabilize at around 30° C. Since thermoelectric coolers work best when thermal gradients are minimized between the heated or cooled object and the heat sink, this improves efficiency of the overall system. When the system shown in FIGS. 11A-11D is operated, the temperature of the two regions of the microfluidic device can be independently controlled. Although the use of a common heat sink may be particularly advantageous, the use of separate heat sinks for different thermoelectric coolers is also compatible with embodiments of the invention.

Figure 12A:
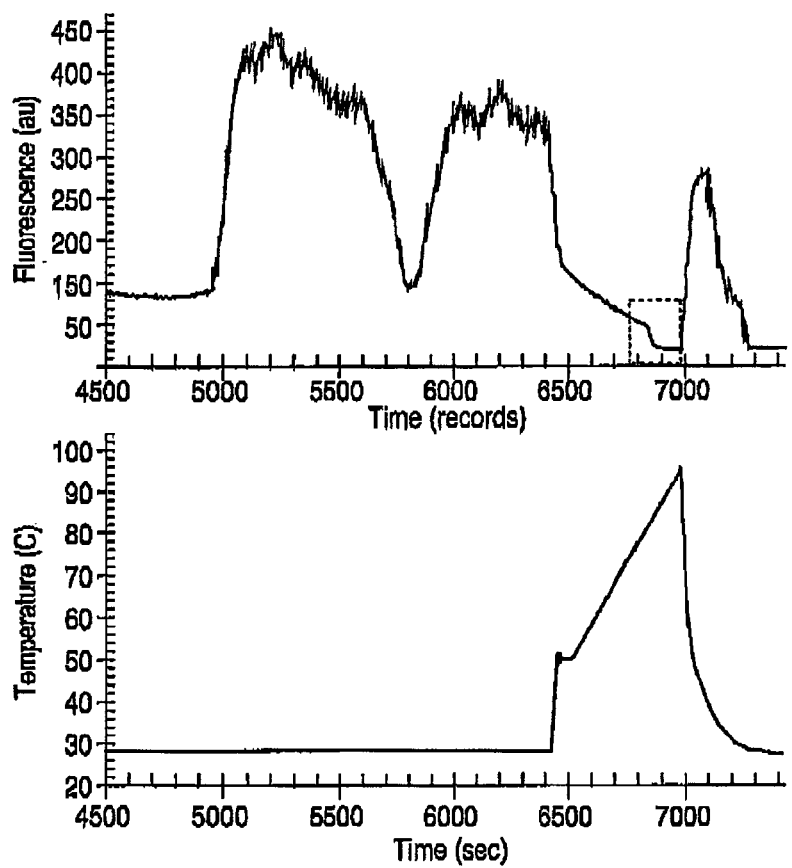
FIGS. 12A-12B show example data from a DNA thermal denaturation (thermal melt) experiment obtained using the microfluidic device shown in FIG. 10.
Figure 12B:
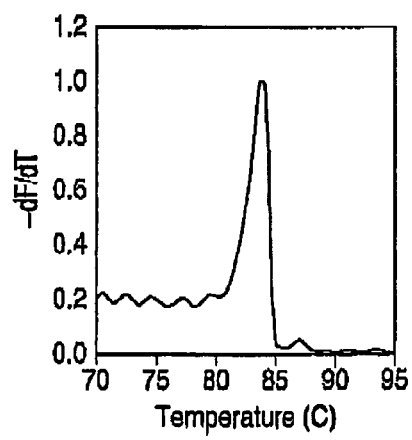

The instrument shown in FIGS. 11A-11D and the microfluidic device shown in FIG. 10 were used to amplify an 85 bp target from genomic DNA in the presence of the DNA binding dye SYBR Green I, which is fluorescent when bound to double-stranded DNA. In the microfluidic device, the amplification products were subjected to a thermal gradient from 60° C. to 95° C. at a rate of approximately 0.1° C./s. FIG. 12A shows the thermal ramp (below) and the change in fluorescent signal (above) over time. The boxed area in the upper portion of FIG. 12A is the region of the DNA thermal melt. FIG. 12B plots the negative change in fluorescence (dF) divided by the change in temperature (dT) as a function of temperature, for the boxed region in FIG. 12A. The temperature at the single peak in this plot represents the temperature at the midpoint of the DNA denaturation curve, or the T, value for the 85 bp target.

Assay Kits

The present invention also provides kits for conducting the binding assays of the invention. In particular, these kits typically include microfluidic devices, systems, modules and workstations for performing the assays of the invention. A kit optionally contains additional components for the assembly and/or operation of a multimodule workstation of the invention including, but not restricted to robotic elements (e.g., a track robot, a robotic armature, or the like), plate handling devices, fluid handling devices, and computers (including e.g., input devices, monitors, CPU, and the like).

Generally, the microfluidic devices described herein are optionally packaged to include reagents for performing the device's functions. For example, the kits can optionally include any of the microfluidic devices described along with assay components, buffers, reagents, enzymes, serum proteins, receptors, sample materials, antibodies, substrates, control material, spacers, buffers, immiscible fluids, etc., for performing the assays of the invention. In the case of prepackaged reagents, the kits optionally include pre-measured or pre-dosed reagents that are ready to incorporate into the assay methods without measurement, e.g., pre-measured fluid aliquots, or preweighed or pre-measured solid reagents that can be easily reconstituted by the end-user of the kit.

Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes1pumps, or the like (in one embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microbicides/bacteriostats, anticoagulants), the physical stabilization of the material, e.g., through immobilization on a solid support, entrapment in a matrix (i.e., a bead, a gel, etc.), lyophilization, or the like.

The elements of the kits of the present invention are typically packaged together in a single package or set of related packages. The package optionally includes written instructions for carrying out one or more target independent assay in accordance with the methods described herein. Kits also optionally include packaging materials or containers for holding microfluidic device, system or reagent elements.

The discussion above is generally applicable to the aspects and embodiments of the invention described herein. Moreover, modifications are optionally made to the methods and devices described herein without departing from the spirit and scope of the invention as claimed, and the invention is optionally put to a number of different uses including the following:

The use of a microfluidic system containing at least a first substrate and having a first channel and a second channel intersecting the first channel, at least one of the channels having at least one cross-sectional dimension in a range from 0.1 to 500 μm, in order to test the effect of each of a plurality of test compounds on a biochemical system comprising one or more focused cells or particles.

The use of a microfluidic system as described herein, wherein a biochemical system flows through one of said channels substantially continuously, providing for, e.g., sequential testing of a plurality of test compounds.

The use of a microfluidic device as described herein to modulate reactions within microchannels.

The use of electrokinetic injection in a microfluidic device as described herein to modulate or achieve flow in the channels.

The use of a combination of wicks, electrokinetic injection and pressure based flow elements in a microfluidic device as described herein to modulate, focus, or achieve flow of materials, e.g., in the channels of the device.

An assay utilizing a use of any one of the microfluidic systems or substrates described herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

---

The invention claimed is:

1. A system for performing a thermal denaturation analysis of a nucleic acid in a microfluidic device, the system comprising:
   a microfluidic device having at least one microfluidic channel;
   a loading device configured to introduce a fluid comprising the nucleic acid and amplification reagents into the microfluidic channel so that the fluid flows into the channel;
   a heating system in communication with a temperature controller configured to cycle a fluid temperature in at least one portion of the microfluidic channel so that the nucleic acid undergoes amplification; and
   the temperature controller configured to continuously increase a temperature of the fluid containing the amplified nucleic acid in at least one portion of the channel to cause denaturation of the nucleic acid after the amplification is completed;
   a detector configured to measure a detectable property emanating from the fluid containing the amplified nucleic acid in the at least one portion of the microfluidic channel as a function of a continuously increasing temperature, the detectable property being indicative of the extent of denaturation of the nucleic acid, the detectable property decreasing as a nucleic acid molecule denatures in real time, wherein the amplification and the measurement of the detectable property are performed in the same channel, wherein the fluid flow during the amplification is subject to the same flow control as the fluid flow during the thermal melt denaturation; and
   a controller configured to generate a thermal property curve representing the measured detectable property as a function of the continuously increasing temperature and determine a nucleic acid melting temperature based on the thermal property curve.

2. The system of claim 1, wherein the nucleic acid is DNA.

3. The system of claim 1, wherein the loading device comprises a pipettor extending from the microfluidic device and is in communication with the channel.

4. The system of claim 1, wherein the fluid control is limited to controlling a pressure differential between two locations at the microfluidic channel, wherein the amplification portion of the channel and the denaturation portion of the channel are positioned between the two locations along the channel.

5. The system of claim 1, wherein the fluid is stopped in the at least one portion of the channel to perform the amplification followed by the nucleic acid denaturation analysis including measuring the detectable property as a function of a continuously increasing temperature.

6. The system of claim 5, wherein the at least one portion of the channel containing the stopped fluid is in communication with the heating system varying the temperature in the at least one portion of the channel to perform the amplification and the denaturation analysis.

7. The system of claim 5, wherein the temperature of the fluid is continuously increased at a rate in the range of 0.1° C./second to 1° C./second.

8. The system of claim 5, wherein the temperature of the fluid is continuously increased at a rate in the range of 0.01° C./second to 0.1° C./second.

9. The system of claim 5, wherein the temperature of the fluid is continuously increased at a rate in the range of 1° C./second to 10° C./second.

10. The system of claim 1, wherein the fluid continuously flows through the at least one portion of the channel and the amplification and the denaturation analysis are performed in the continuously flowing fluid.

11. The system of claim 10, wherein the at least one portion of the channel containing the continuously flowing fluid is in communication with the heating system varying the temperature in the at least one portion of the channel to perform the amplification and the denaturation analysis including measuring the detectable property as a function of a continuously increasing temperature.

12. The system of claim 1, wherein the cycling of the temperature of the at least one portion of the microfluidic channel comprises varying an electric current used to joule heat the at least one portion.

13. The system of claim 1, wherein the cycling of the temperature of the at least one portion of the microfluidic channel comprises varying the temperature of the at least one portion using a non-joule heating system.

14. The system of claim 13, wherein the non-joule heating system comprises placing the at least one portion of the microfluidic channel in thermal contact with a thermal block, wherein the temperature is cycled by varying the temperature of the thermal block.

15. The system of claim 13, wherein the non-joule heating system comprises passing an electric current through resistive heating elements in thermal contact with the at least one portion of the microfluidic channel, wherein the temperature is cycled by varying the current passing through the resistive heating elements.

16. The system of claim 15, wherein the resistive heating elements are fabricated onto a surface of the microfluidic device.

17. The system of claim 1, wherein the amplification is performed by using a technique selected from a group consisting of: PCR and LCR.

18. The system of claim 1, wherein the amplification reagents include primers, a thermostable polymerase, and nucleotides.

19. The system of claim 1, wherein the detectable property comprises fluorescence.

20. The system of claim 19, wherein the fluorescence is generated by FRET or a molecular beacon.

21. The system of claim 19, wherein the fluorescence is generated by a fluorescent dye, and wherein the amount of fluorescence generated by the fluorescent dye is indicative of the extent of thermal denaturation of the nucleic acid.

22. The system of claim 21, wherein the fluorescent dye is selected from the group consisting of: an intercalating dye, ethidium bromide, a minor groove binding dye, and a SYBR green dye.

23. The system of claim 1, wherein the detectable property is selected form the group consisting of: fluorescence polarization, UV absorbance.

24. The system of claim 1, wherein the detectable property is selected from the group of heat capacity, electrical resistance, and dielectric properties.

25. The system of claim 1, wherein the system further comprises:
    a fluid comprising a molecule of a known melt temperature (Tm), the fluid flowing through the channel, wherein a physical parameter that correlates with the temperature within the channel is being varied,
    a detector configured to measure a value of the detectable property of the molecule as a function of the parameter, wherein the thermal property curve for the molecule is generated; and
    a processor configured to determine the values of the detectable property and the parameter at the point in the thermal property curve that corresponds to the Tm of the molecule and derive the fluid temperature in the channel of microfluidic device based upon the determined values of the detectable property and the parameter.

26. The system of claim 25, wherein the molecule of known Tm is selected from the group consisting of: a nucleic acid with a known sequence, biotin, biotin-4-fluorescein, fluorescein biotin, avidin, streptavidin, and neutravidin.

27. The system of claim 25, wherein the physical parameter is selected from the group consisting of: the temperature of a thermal block in thermal contact with the channel, the current applied to the fluid in order to joule heat the fluid, and the current applied to a resistive heating element in thermal contact with the channel.

28. A system for performing a thermal denaturation analysis of a nucleic acid in a microfluidic device, the system comprising:
    a microfluidic device having at least one microfluidic channel;
    a loading device configured to introduce a fluid comprising the nucleic acid and amplification reagents into the microfluidic channel so that the fluid flows into the channel;
    a heating system controlled by a temperature controller, wherein the temperature controller is configured:
        (a) to cycle a fluid temperature in at least one portion of the microfluidic channel so that the nucleic acid undergoes amplification; and
        (b) after the amplification is completed, continuously increase a temperature of the fluid containing the amplified nucleic acids in the at least one portion of the channel to cause denaturation of the nucleic acids; and
    a detector configured to measure a detectable property emanating from the fluid containing the amplified nucleic acids in the at least one portion of the microfluidic channel as a function of the continuously increasing temperature to generate a thermal property curve, wherein the detectable property decreases as a nucleic acid molecule denatures in real time.

* * * * *